United States Patent [19]

Piazza et al.

[11] Patent Number: 5,858,694
[45] Date of Patent: Jan. 12, 1999

[54] METHOD FOR IDENTIFYING COMPOUNDS FOR INHIBITION OF CANCEROUS LESIONS

[75] Inventors: Gary A. Piazza, Doylestown; Rifat Pamukcu, Spring House, both of Pa.; W. Joseph Thompson, Mobile, Ala.

[73] Assignee: Cell Pathways, Inc., Horsham, Pa.

[21] Appl. No.: 866,027

[22] Filed: May 30, 1997

[51] Int. Cl.[6] ..................................................... C12Q 1/44
[52] U.S. Cl. ............................................ 435/19; 435/184
[58] Field of Search ............................. 435/4, 6, 15, 19, 435/184, 196; 424/9.1, 9.2; 436/64

[56] References Cited

U.S. PATENT DOCUMENTS

| | | | |
|---|---|---|---|
| 4,983,514 | 1/1991 | Weithmann et al. | 435/29 |
| 5,389,527 | 2/1995 | Beavo et al. | 435/69.1 |
| 5,393,755 | 2/1995 | Neustadt et al. | 514/233.2 |
| 5,401,774 | 3/1995 | Pamukcu et al. | 514/569 |
| 5,439,895 | 8/1995 | Lee et al. | 514/63 |
| 5,498,608 | 3/1996 | Johnson et al. . | |
| 5,521,191 | 5/1996 | Greenwald | 514/262 |
| 5,570,683 | 11/1996 | Zapol . | |
| 5,624,808 | 4/1997 | Thompson et al. . | |
| 5,626,838 | 5/1997 | Cavanaugh, Jr. . | |
| 5,637,465 | 6/1997 | Trauth . | |
| 5,637,486 | 6/1997 | Tomei . | |
| 5,643,959 | 7/1997 | Pamukcu et al. . | |
| 5,652,131 | 7/1997 | Beavo et al. . | |
| 5,702,936 | 12/1997 | Beavo et al. | 435/196 |

FOREIGN PATENT DOCUMENTS

| | | |
|---|---|---|
| 0291873B1 | 5/1988 | European Pat. Off. . |
| 0260527B1 | 4/1992 | European Pat. Off. . |
| WO 92/17610 | 10/1992 | WIPO . |
| WO 94/28144 | 12/1994 | WIPO . |
| WO 96/20281 | 7/1996 | WIPO . |
| WO 96/40985 | 12/1996 | WIPO . |
| WO 97/14679 | 4/1997 | WIPO . |

OTHER PUBLICATIONS

Boopathy, R. and A. S. Balasubramanian, "Purification and Characterization of Sheep Platelet Cyclo–oxygenase," *Biochem. J.*, vol. 239, pp. 371–377. (1986).

Brooker, G. et al., "Radioimmunoassay of Cyclic AMP and Cyclic GMP," *Advances in Cyclic Nucleotide Research*, Raven Press, New York, vol. 10, pp. 1–33. (1979).

Collins, S. J. et al., "Normal Functional Characteristics of Cultured Human Promyelocytic Leukemia Cells (HL–60) After Induction of Differentiation by Dimethylsulfoxide," *The Journal of Experimental Medicine*, vol. 149, pp. 969–974. (1979).

Duke, R. C. and J. J. Cohen, "Morphological and Biochemical Assays of Apoptosis," *Current Protocols in Immunology*, John Wiley & Sons, New York, eds. J.E. Coligan, et al., sections 3.17.1–3.17.16. (1992).

Fogh, J. and G. Trempe, "New Human Tumor Cell Lines," *Human Tumor Cells In Vitro*, Plenum Press, New York, pp. 115–141. (1975).

Kargman, S et al., "Translocation of HL–60 Cell 5–Lipoxygenase," *J. Biol. Chem.*, vol. 266, No. 35, pp. 23745–23752. (1991).

Mehta, R. G. and R. C. Moon, "Effects of 12–0–tetradecanoylphorbol–13–acetate on Carcinogen–induced Mouse Mammary Lesions in Organ Culture," *Cancer Research*, vol. 46, pp. 5832–5835. (1986).

Mitchell, J. A. et al., "Selectivity of nonsteroidal antiinflammatory drugs as inhibitors of constitutive and inducible cyclooxgenase," *Proc. Natl. Acad. Sci. USA*, vol. 90, pp. 11693–11697. (1994).

Piazza, G. A. et al., "Antineoplastic Drugs Sulindac Sulfide and Sulfone Inhibit Cell Growth by Inducing Apoptosis," *Cancer Research*, vol. 55, pp. 3110–3116. (1995).

Seibert, A. F. et al., "Reversal of Increased Microvascular Permeability Associated With Ischemia–reperfusion: Role of cAMP," *J. Applied Physiol.*, pp. 389–395. (1992).

Skehan, P. et al., "New Colorimetric Cytotoxicity Assay for Anticancer–Drug Screening," *J. Nat. Cancer Inst.*, vol. 82, No. 13, pp. 1107–1112. (1990).

Steiner, A. L. et al., "Radioimmunoassay for Cyclic Nucleotides," *J. Biol. Chem.*, vol. 247, No. 4, pp. 1106–1113. (1972).

Thompson, H. J. et al., "Inhibition of Mammary Carcinogenesis in Rats by Sulfone Metabolite of Sulindac," *J. Nat. Cancer Inst.*, vol. 87, No. 16, pp. 1259–1260. (1995).

Thompson, W. J. et al., "Assay of Cyclic Nucleotide Phosphodiesterase and Resolution of Multiple Molecular Forms of the Enzyme," *Advances in Cyclic Nucleotide Research*, Raven Press, New York, vol. 10, pp. 69–92. (1979).

Waddell, W. R. and R. W. Loughry, "Sulindac for Polyposis of the Colon," *J. Surg. Oncol.*, vol. 24, pp. 83–87. (1983).

Tsou, K.C. et al.; Histochemical Journal, 6 (1974) pp. 327–337.

Tsou, K.C. et al.; Cancer Research 33: 2215 2217, (Oct. 1973).

Tsou, K.C. et al.; Cancer Research 50:191–196, (1982).

Tsou, K.C. et al,; Cancer Reseach 45:209–213, (1980).

Tsou, K.C. et al,; Journal of the National Cancer Institute, vol. 51, No. 6, (Dec. 1973).

Tsou, K.C. et al.; Oncology 37: 381–385 (1980).

Tsou, K.C. et al.; Journal of Clinical Hematology And Oncology., vol. 10, No. 1, (Jan. 1980).

Morley, Debra J. et al.; The Journal of Histochemistry and Cytochemistry, vol. 35, No. 1, pp. 75–82 (1987).

(List continued on next page.)

*Primary Examiner*—Ralph Gitomer
*Attorney, Agent, or Firm*—Brinks Hofer Gilson & Lione

[57] ABSTRACT

This invention provides a method to identify compounds potentially useful for the treatment of neoplasia in mammals. The phosphodiesterase inhibitory activity of a compound is determined along with COX inhibitory activity. Growth inhibitory and apoptosis inducing effects on cultured tumor cells are also determined. Compounds that exhibit phosphodiesterase inhibiton, growth inhibition and apoptosis induction, but not substantial prostaglandin inhibitory activity, are desirable for the treatment of neoplasia.

26 Claims, 13 Drawing Sheets

OTHER PUBLICATIONS

Cancer Research 58: 914–920 (Mar. 1, 1998) Sugita M.
Beavo, Joseph; Physiological Reviews, vol. 75, No. 4, (Oct. 1995).
Beltman et al.; Molecular Pharmacology, 47:330–339 (1995).
Essayan et al.; The Journal of Immunology, 153: 3408 (1994).
Beavo et al.; Molecular Pharmacology, 46:399–405 (1994).
Qiao et al.; Biochemical Pharmacology, vol. 55, pp. 53–64 (1998).
Japan. J. Pharmacol. 46, 373–378 (1988) Takagi K.
Tulshian et al.; Journal of Medicinal Chemistry vol. 36., No. 9; pp. 1210–1220 (1993).
Pfizer Inc.; BioCentry, The Bernstein Report on BioBusiness, p. A4 (Jul. 14, 1997).
Terrett, Nicholas et al.; Bioorganic & Medicinal Chemistry Letters, vol. 6, No. 15, pp. 1819–1824 (1996).
Silvola et al.; Agents and Actions, vol. 12.4 (1982).
Drees et al.; Cancer Research, 53:3058–3061, (Jul. 1, 1973).
Wilhelm et al.; Syntex Research, 8–Aryl Quinolines As Potent and Selective Type Iv Phosphodiesterase Inhibitors. No Date Avail.
Thompson, W. Joseph; Pharmac. Ther. vol. 51, pp. 13–33 (1991).
Yasumoto et al.; Biochemical Pharmacology, vol. 43, No. 10. pp. 2073–2081 (1992).
Villone et al.; vol. 8, pp. 1181–1188 (Nov. 1997).
Tortora et al.; Cancer Research 57:5107–5111 (Nov. 15, 1997).
Sandberg et al.; Biochemistry vol. 279, pp. 521–527 (1991).
Vintermyr et al.; Experimental Cell Research vol. 206. pp. 157–161 (1993).
McConkey et al.; The Journal of Immunology vol. 145 No. 4 pp. 1227–1230 (1990).
Dowd et al,; Molecular and Cellular Biology vol. 12, No. 8 pp. 3600–3608 (1992).
Botelho et al,; Methods in Enzymology, vol. 159 pp. 159–171 1988.
Kizaki et al.; The Journal of Biological Chemistry vol. 265, No. 9 pp. 5280–5284 (Mar. 25, 1990).
Kemp et al.; Cancer Research 35:2440–2445 (Sep. 1975).
Willey et al.l; Journal of Cellular Physiology 124:207–212 (1985).
Chastre et al.; FEBS Letters vol. 188, No. 2 pp. 197–204 (Sep. 1985).
Busse et al.; Oncology 48:196–201 (1991).
Tortora et al.; Clinical Cancer Research vol. 1, pp. 46–56 (Jan. 1995).
Lando et al.; Cancer Research 50:722–727 (Feb. 1, 1990).
Quedraogo et al.; Br. J. Pharmacol 111. pp. 625–631 (1994).
Just et al.; Biochemical Pharmacology vol. 42, No. 2. pp. 285–294 (1991).
Gruol et al.; Molecular Endocrinology vol. 7, No. 1. pp. 104–113 (1993).
Ojeda et al.; Induction of Apoptosis in Thymocytes: New Evidence for an Interaction of PKC and PKA Pathways 1995.
Lanotte et al.; Journal of Cellular Physiology 146:73–80 (1991).
Krett et al.; Clinical Cancer Research vol. 3. pp. 1781–1787 (Oct. 1997).
Nesbitt et al.; The Journal of Biological Chemistry vol. 251, No. 8. pp. 2344–2352 (Apr. 25, 1976).
Gennari et al.; Journal of Clinical Pathology vol. 31 pp. 735–741 (1978).
Orbo et al.; Anticancer Research 75: pp. 1905–1910 (1995).
Orbo et al.; Gynecologic Oncology vol. 52. pp. 320–325 (1994).
Duttagupta et al.; Cancer Research vol. 42. pp. 2938–2942 (Jul. 1982).
Barsony, Julie; The Second International Forum on Calcified Tissue and Bone Metabolism pp. 18–21 (1993).
Wedner et al.; The Journal of Immunology vol. 115, No. 6. pp. 1682–1687 (Dec. 1975).
Coffey et al.; The Journal of Immunology vol. 119, No. 4. pp. 1387–1394 (Oct. 1977).
Pilz et al.; Research Communication vol. 9. pp. 552–558 (Apr. 1995).
Tsang et al.; Science vol. 272. (May 17, 1996).
Appel, Richard G.; The American Physiological Society. pp. E312–318 (1990).
Keilbach et al.; FEBS EJB 92 0649. pp. 467–473 (May 12, 1992).
Hadden et al.; Proc. Nat. Acad. Sci. USA vol. 69, No. 10, pp. 3024–3027 (Oct. 1972).
Orbo et al.; International Journal Cancer; vol. 55. pp. 957–962 (1993).
Tien et al.; vol. 269, No. 1. pp. 51–54 (1994).
Tang et al.; European Journal of Pharmacology; Molecular Pharmacology Section 268. pp. 105–114 1994).
Remme et al.; J. Cardiovasc. Pharmacol. vol. 24, No. 5 (Nov. 1994) AB only.
Weiss et al.; Clinical Exp. Pharmacol.Physiol. vol. 21, No. 8 (Aug. 1994) AB only.
Lee et al.; J. Pharmacol.Exp.Ther. vol. 270, No. 3 (Sep. 1994) AB only.
Eckly et al.; Br. J. Pharmacol. vol. 113, No. 2 (Oct. 1994) AB only.
Nankervis et al.; J. Cardiovasc.Pharmacol. vol. 24, No. 4 (Oct. 1994) AB only.
Sugioka et al.; Maunyn Schmiedebergs Arch. Pharmacol. vol. 350, No. 3 (Sep. 1994) AB only.
Schroeder et al.; Arzneimittelforschung; vol. 44, No. 8 (1994) AB only.
Kishi et al.; J. Cardiovasc. Pharmacol. vol. 24, No. 3 (Sep. 1994) AB only.
Peikin et al.; The Journal of Biological Chemistry. vol. 254, No. 12. pp. 5321–5327 (Jun. 25, 1979).
Brüne et al.; Molecular Pharmacology. vol. 39. pp. 671–678 ((1991).
Hoosein et al.; Experimental Cell Research vol. 186. pp. 15–21 (1990).
Maurice et al.; Analytical Biochemistry vol. 215. pp. 110–117 (1993).
Cornwell et al.; American Journal Physiology. vol. 267 pp. C1405–1413 (1994).
Bäummer et al.; European Journal of Pharmacology vol. 273. pp. 295–298 (1995).
Koga et al.; The Journal of Biological Chemistry. vol. 269, No. 15. pp. 11640–11647 (Apr. 15, 1994).
Kunzelmann et al.; Pflügers Arch. 421. pp. 238–246 (1992).
Srivastava et al.; Clinical Cancer Research. vol. 4. pp. 755–761 (Mar., 1998).
McAllister et al.; The Journal of Biological Chemistry. vol. 268, No. 20. pp. 22863–22873 (Oct. 25, 1993).
Kanba et al.; Journal of Neurochemistry. vol. 57. pp. 2011–2015 (1991).

Wolin et al.; The Journal of Biological Chemistry. vol. 257. No. 22. pp. 13312–13320. (Nov. 25, 1982).
Schulz et al.; The Journal of Biological Chemistry. vol. 267, No. 23. pp. 16019–16021 (Aug. 15, 1992).
Schulz et al.; Cell. vol. 63. pp. 941–948 (Nov. 30, 1990).
Currie et al.; Proc. Natl. Acad. Sci. USA. vol. 89. pp. 947–951 (Feb. 1992).
Butt et al.; The Journal of Biological Chemistry vol. 269, No. 20. pp. 14509–14517 (May 20, 1994).
Cohen et al.; The American Society for Clinical Investigation, inc. vol. 97, No. 1. pp. 172–179 (Jan. 1996).
Pfeifer et al.; Science vol. 274. pp. 2082–2086 (Dec. 20, 1996).
Hunt et al.; Clinical Science vol. 58. pp. 463–467 (1980).
Peracchi et al.; Cancer vol. 54. pp. 3028–3034 (1984).
Barsony et al.; Proc. Natl. Acad. Sci. USA vol. 87. pp. 1188–1192 (Feb.1990).
Dimmeler et al.; JEM vol. 185, No. 4 pp. 601–608(Feb. 17, 1997).
Lincoln et al.; FASEB J. vol. 7. pp. 328–338 (1993).
Sonnenburg et al.; Advances in Pharmacology, vol. 26. pp. 87–114 (1994).
Osborne et al.; Science, vol. 277. pp. 834–836 (Aug. 8, 1997).
Turner et al.; Eur. J. Gynaec. Oncol.—0392–2936 XI, n. 6, 1990.
Sugita et al.; Cancer Research 58, pp. 914–920 (Mar. 1, 1998).
Lichtner et al.; Cancer Research 47, pp. 1870–1877 (Apr. 1, 1987).
Sedlak, Bonnie Joy, Ph.D.; Genetic Engineering News, p. 8 (Jan. 1, 1996).
Fingert et al.; Cancer Research, vol. 36, pp. 2463–2467 (May 1986).
Fingert et al.; Cancer Reseach, vol. pp. 4375–4381 1988.
Hatmi et al.; Prostaglandins vol. 43. pp. 457–472 (1992).
Delpy et al.; British Journal of Pharmacology vol. 118. pp. 1377–1384 (1996).
Yu et al.; Biochem J. vol. 306 pp. 787–792 (1995).
Hagiwara et al; Mie University School of Medicine, Tsu 514. Japan 1983.
Burns et al.; Biochem J. vol. 283. pp. 487–491 (1992).
Janik et al.; Cancer Research vol. 40. pp. 1950–1954 (Jun. 1980).
Prasad et al.; Experimental Cell Research vol. 73. pp. 436–440 (1972).
Gillespie et al.; Molecular Pharmacology; vol. 36. pp. 773–781 1989.
Wells et al.; Methods in Enzymology; vol. 139. pp. 489–497 1988.
Tisdali et al.; Biochemical Pharmacology; vol. 24. pp. 211–217 (1975).
Yamashita et al.; J. Pharm Pharmacol; vol. 45. pp. 530–534 1993.
Ichimura et al.; Biochem J. vol. 316. pp. 311–316 (1996).
Sekut et al.; Clin. Exp Immunol; vol. 100. pp. 126–132 (1995).
Silver et al.; The Journal of Pharmacology and Experimental Therapeutics; vol. 271, No. 3, pp. 1143–1149 (1991).
Williams et al.; The Journal of Biological Chemistry; vol. 271, No. 21. pp. 12488–12495 (May 24, 1996).
Saeki et al.; The Journal of Pharmacology and Experimental Therapeutics; vol. 272, No. 2. pp. 825–831 (1995).
Dundore et al.; European Journal of Pharmacology, vol. 249. pp. 293–297 (1993).
Kodama et al.; European Journal of Pharmacology vol. 263. pp. 93–99 (1994).
Flores et al.; American Journal of Physiology; vol. 233, No. 6. pp. 1392–1397 (Dec. 1972).
Biddle et al.; Patholocie Biologie; vol. 32, No. 1. pp. 9–13 (1984).
Baba et al.; J. Med. Chem. vol. 39. pp. 5176–5182 (1996).
Tatsuta et al.; Oncology Reports; vol. 1. pp. 717–721 (1994).
Hagiwara et al.; The Journal of Pharmacology and Experimental Therapeutics; vol. 228, No. 2 (1983).
Miyahara et al.; European Journal of Pharmacology; vol. 284 pp. 25–33 (1995).
Genieser et al.; Carbohydrate Research; vol. 234. pp. 217–235 (1992).
Takase et al.; J. Med. Chem. vol. 36, pp. 3765–3770 (1993).
Lee et al.; J. Med. Chem. vol. 38, pp. 3547–3557 (1995).
Souness et al.; Br. J. Pharmacol. vol. 98. pp. 725–734 (1989).
Czamiecki et al.; Annual Reports of Medical Chemistry vol. 31. pp. 61–70 (1996).
Clack et al.; J. Med. Chem. vol. 37. pp. 2406–2410 (1994).
Takase et al.; J. Med. Chem. vol. 37, pp. 2106–2111 (1994).
Xia et al.; J. Med. Chem. vol. 40, pp. 4372–4377 (1997).
Ahn et al.; J. Med. Chem. vol. 40, pp. 2196–2210 (1997).
Sheppard et al.; Advances in Cyclic Nucleotide Research, vol. 1, pp. 103–112 (1972).
Zurbonsen et al.; Biochemical Pharmacology, vol. 53, pp. 1141–1147 (1997).
Kangasaho et al.; Agents and Actions, vol. 12, pp. 516–520 (1982).
Howell, Leonard L.; The Journal of Pharmacology and Experimental Therapeutics, vol. 266, No. 2. pp. 894–903 (1993).
Schilling et al.; Analytical Biochemistry vol. 216. pp. 154–158 (1994).
Daniels et al.; Analytical Biochemistry, vol. 236. pp. 367–369 (1996).
Thompson et al.; Advances in Cyclic Nucleotide Research, vol. 10. pp. 69–92 (1979).
Hiratsuka, Toshiaki; The Journal of Biological Chemistry, vol. 257, No. 22, pp. 13354–13358 (1982).
Whalin et al.; Molecular Pharmacology, vol. 39, pp. 711–717 1991.
Murashima et al.; Biochemistry, vol. 29, pp. 5285–5292 (1990).
Wu et al.; The Journal of Biological Chemistry, vol. 272, No. 23, pp. 14860–14866 (Jun. 6, 1997).
Tenor et al.; Clinical and Experimental Allergy, vol. 25, pp. 625–633 (1995).
Russell et al.; The Journal or Biological Chemistry; vol. 248, No. 16. pp. 5835–5840 (1973).
Pledger et al.; Journal of Cyclic Nucleotide Research, vol. 1. pp. 251–259 (1975).
Pledger et al.; Nature New Biology; vol. 256 pp. 729–731 (Aug. 28, 1975).
Hait et al.; Biochimica et Biophysica Acta, 497. pp. 86–100 (1977).
Martins et al.; The Journal of Biological Chemistry, vol. 257, No. 4, pp. 1973–1979 (Feb. 25, 1982).
Groppi et al.; The Journal of Biological Chemistry, vol. 258, No. 16, pp. 9717–9723 (Aug. 25, 1983).
Bertram et al.; Cancer Research vol. 45, pp. 1946–1952 (May 1985).
Sheppard, J.R.; Nature New Biology vol. 236, pp. 14–16 (Mar. 1, 1972).

Whalin et al.; Second Messengers and Phosphorproteins, vol. 12(5&6), pp. 311–325 (1988–89).

King et al.; Cancer Research, vol. 38, pp. 3879–3885 (Nov. 1978).

Hait et al.; Nature, vol. 259 pp. 321–323 (Jan. 29, 1976).

Weiss et al.; Analytical Biochemistry 1952 rest of cite unavail.

Abstract; Murnane, JP; Cancer & Metastatis Reviews. vol. 14(1), pp. 17–29 (Mar. 1995).

Abstract; Aharoni; Experimental Cell Research, vol. 218(1), pp. 271–282 (May 1995).

Abstract; Beauvais et al.; FEBS Letters; vol. 361(2–3), pp. 229–232 (Mar. 20, 1995).

Abstract; Palayoor et al.; Radiation Research, vol. 141(3), pp. 235–243 (Mar. 1995).

Abstract; Zhen et al.l; Radiation Research, vol. 141(2), pp. 170–175 (Feb. 1995).

Demarcq et al.; Cell Growth & Differentiation vol. 5(9) pp. 983–993 (Sep. 1994).

Abstract; Lock et al.; Cancer Research vol. 54(18) pp. 4933–4939 (Sep. 15, 1994).

Abstract; Shinomiya et al.; Experimental Cell Research vol. 210(2), pp. 236–242 (Feb. 1994).

Abstract; Piacentini et al.; FEBS Letters vol. 320(2) pp. 150–154 (Apr. 5, 1993).

Abstract; Traganos et al.; Cancer Research vol. 53(19) pp. 4613–4618 (Oct. 1, 1993).

Abstract; Belizario et al.; British Journal of Cancer vol. 67(6) pp. 1229–1235 (Jun. 1993).

Pledger et al.; J. Cell Physiol. vol. 100, pp. 497–508 (1979).

Hait et al.; Molecular Pharmacology, vol. 16. pp. 851–864 1979.

Menahan et al.; Journal of Cyclic Nucleotide Research. vol. 2, pp. 417–425 (1976).

Epstein et al.; Advances in Cyclic Nucleotide and Protein Phosphorylation Research, vol. 16. pp. 303–324 (1984).

Lynch et al.; Biochemical and Biophysical Research Communications vol. 65, No. 3. pp. 1115–1122 (1975).

Uzunov et al.; Science, vol. 180 pp. 305–306 (Dec. 1972).

Epstein et al.; Cancer Res. 37(11), 1997 pp. 4016–4023.

Sheng et al.; J. Clinical Investigation 99(9):2254–2259 (1997).

Tsujii et al.; PNAS 94: 3336–3340 (1997).

Zurbonsen et al.; Biochemical Pharmacology 53:1141–1147 (1997).

Makaryan, A.P. et al., Laboratornoe Delo, Cyclid Nucleotides in Patients with Malignant Neoplasms of the Colon, vol. 8, pp. 31–33 (1991).

Nicholson et al.; Trends in Pharmaceutical Sciences, vol. 12: 19–27 (Jan. 1991).

Radomski et al.; Cancer Research 51: 6073–6078 (1991).

DuBois; Gastroenterology 108 (4):1310–1314 (1995).

Sano et al.; Cancer Research 55: 3785–3789 (1995).

DuBois et al.; J. Gastroenterology 31: 898–906 (1996).

Campagnolo et al.; J. Neurooncology 31, (1–2): 123–127 (1997).

Kinoshita K., Structure of Sporostatin, J of Antibiotics 50(11)961–964, 1997.

Molnar–Kimber K., Modulation of TNF alpha and IL–1beta from Endotoxin–Stimulated Monocytes by Selective PDE Isozyme Inhibitors, Agents Actions 39(C77–79), 1993.

Curtis–Prior, P., Cyclic Nucleotide Phosphodiesterase Activity of Human Normal and Carcinomatous Lung Tissue, Lancet, 1224–5, Dec. 1976.

Jiang, X., Inhibition of Calmodulin Dependent Phosphodiesterase Induces Apoptosis in Human Leukemic Cells, Proc Natl Acad Sci USA vol. 93, pp. 11236–11241, Oct. 1996.

Fontana J., Inhibition of Human Mammary Carcinoma Cell Proliferation by Retinoids and Intracellular cAMP Elevating Compounds, Jnci 78(6)1107–1112, Jun. 1987.

Torphy T., Phosphodiesterase Inhibitors, Thorax, vol. 46 pp. 512–523, 1991.

Coste H., Characterization of a Novel Potent and Specific Inhibitor of Type V Phosphodiesterase, Biochemical Pharm 50(10)1577–1585, 1995.

Terrett N., Sildenafil (Viagra) . . . Bioorganic & Medicinal Chemistry Letters, 6(15)1819–1824, 1996.

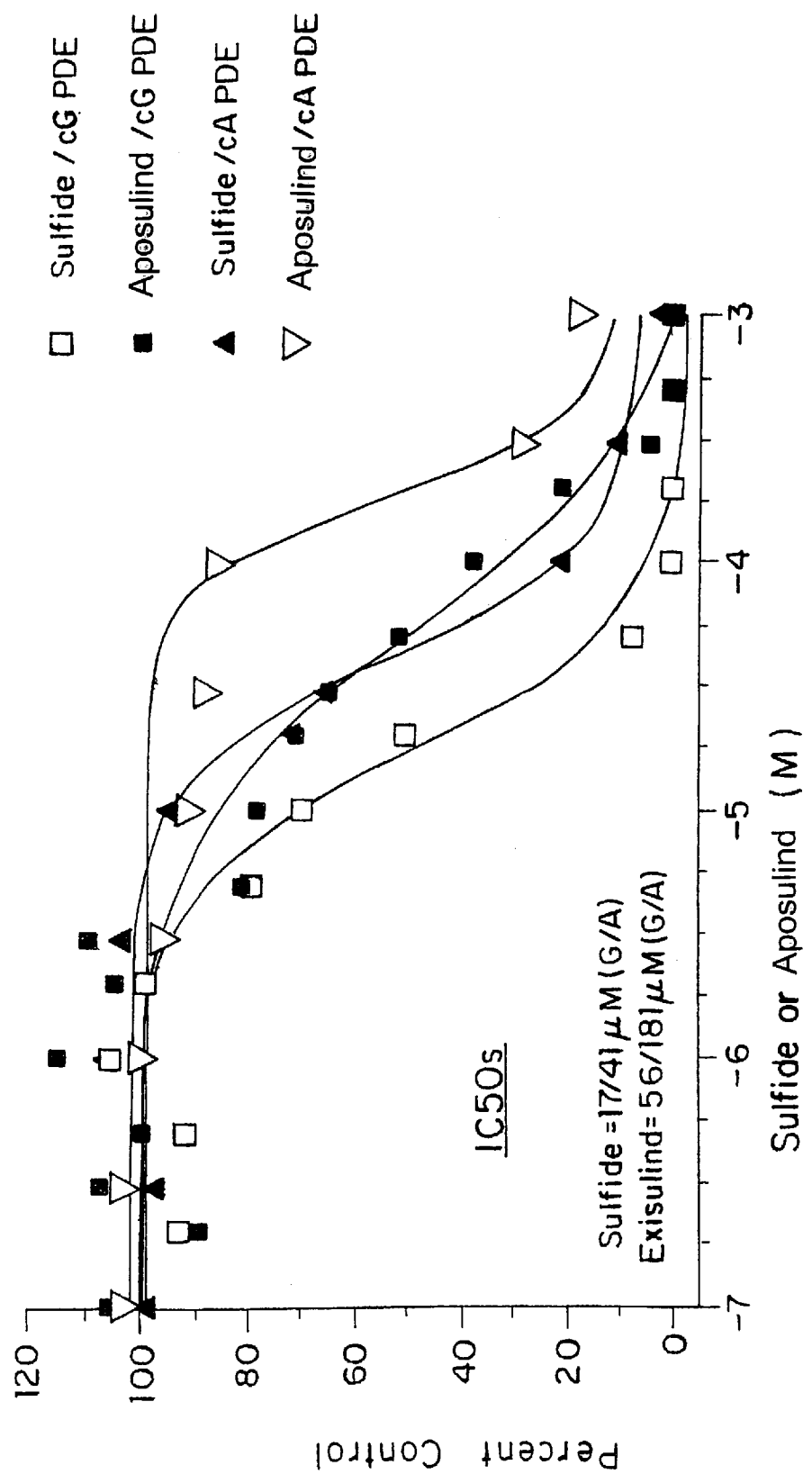

METHOD FOR IDENTIFYING COMPOUNDS FOR INHIBITION OF CANCEROUS LESIONS

BACKGROUND OF THE INVENTION

1. Field of the Invention

This invention provides a method for identifying compounds potentially useful for the treatment and prevention of pre-cancerous and cancerous lesions in mammals.

2. Discussion of the Background

Familial adenomatous polyposis ("FAP") is an inherited condition where the victim's colon contains many polyps—virtually uncountable in most instances. Because such patients develop so many polyps—each of which has a significant risk of developing into a cancer—the typical treatment is surgical removal of the colon. In about 1983, Waddell discovered that the non-steroidal anti-inflammatory drug ("NSAID") sulindac would cause colonic polyps (a type of pre-cancerous lesion) to regress and prevent their recurrence when that drug was administered to patients with FAP. Waddell's experience with sulindac in FAP patients has been confirmed in several subsequent studies. Unfortunately, since sulindac aggravates the digestive tract (not to mention side effects involving kidney and interference with normal blood clotting) of patients to whom it has been chronically administered, it is not a practical treatment for FAP or any other cancer or precancerous indication requiring long-term administration.

Waddell originally hypothesized that the mechanism of action of sulindac on colonic polyps involved the inhibition of the synthesis of prostaglandin (PG). (Waddell, W. R. et al., "Sulindac for Polyposis of the Colon," *Journal of Surgical Oncology*, 24:83–87, 1983). Prostaglandin ("PG") synthesis inhibition results from the inhibition of cyclooxygenase (COX) caused by NSAIDs. A common benefit of NSAIDs is the reduction of inflammation, which is known to be caused by the reduction of PG levels. Since NSAIDs are known to inhibit COX, which inhibits PG synthesis, it is widely believed that the regression of colonic polyps is attributed to this property. In fact, notwithstanding recent discoveries to the contrary, it has become conventional wisdom that administration of an inhibitor of PG synthesis (e.g., an NSAID) to an FAP patient will result in the regression of colonic polyps due to a reduction of PG levels.

Recent discoveries, however, are leading scientists in a completely different direction—that it is not necessary to inhibit COX to treat FAP patients successfully. Pamukcu et al., in U.S. Pat. No. 5,401,774, disclosed that sulfonyl derivatives of sulindac, that were previously reported to be inactive as PG synthesis inhibitors (and therefore not an NSAID or an anti-inflammatory compound) unexpectedly inhibited the growth of a variety of tumor cells, including colon polyp cells. These sulfonyl derivatives have proven effective in rat models of colon carcinogenesis, and one variant (now referred to as aposulind) has proven effective in preliminary human clinical trials with FAP patients.

The importance of this discovery—and the de-linking of anti-cancer activity and COX inhibition—cannot be overstated. If those two phenomena were related, there would be little hope for a safe NSAID therapy for FAP patients because the side effects of NSAIDs, such as gastric irritation, are also caused by COX inhibition. Prostaglandins play a protective function in the lining of the stomach. When NSAIDs are administered, COX is inhibited and PG levels are reduced: gastric irritation is a common result. Those side effects may not manifest themselves in short-term (acute) NSAID therapy. However, during long-term (chronic) NSAID therapy, gastric irritation, bleeding and ulceration are very common. In significant numbers of cases, NSAID therapy must be stopped due to the severity of those side effects and other potentially lethal side effects. Furthermore, the severity of such side effects increases with age, probably because natural PG levels in gastric mucosa falls with age. Thus, useful compounds for treating neoplastic lesions should desirably inhibit tumor cell growth, but should not inhibit COX.

Conventional methods for finding (i.e. screening) compounds may be used to find improved compounds that inhibit tumor cell growth alone. Under this scenario, drugs may be screened using in vitro models. But conventional in vitro compound screening methods could pass many compounds that later are shown to be ineffective in animal models because of the cytotoxic effects of the compounds. Animal model studies are time consuming and expensive. Therefore, a more precise in vitro screening method that provides information on selectivity for treating precancer or cancer is needed to screen compounds prior to animal testing. This will allow for greater precision and efficiency whereby highly effective and safe compounds can be identified prior to animal testing.

Presently, rational drug discovery methods are being applied in the pharmaceutical industry to improve methods for identifying clinically useful compounds. Typically, rational drug discovery methods relate to a "lock and key" concept whereby structural relationships between a therapeutic target molecule (lock) and pharmaceutical compounds (key) are defined. Such methods are greatly enhanced by specialty computer software that accesses databases of compounds to identify likely geometric fits with the target molecule. Unfortunately, to use these systems, one has to have insight to the target molecule (lock). The target may be an enzyme, a protein, a membrane or nuclear receptor, or a nucleic acid, for example.

In complex diseases, such as cancer, scientists have identified a number of potential targets. However, many of the drugs available for the treatment of cancer are non-specific and cause toxicity to normal tissues. Greater understanding of the mechanisms involved in cancer may lead scientists on the path towards designing more specific anti-neoplastic drugs.

SUMMARY OF THE INVENTION

This invention relates to a novel in vitro method for screening test compounds for their ability to treat and prevent neoplasia, especially pre-cancerous lesions, safely. In particular, the present invention provides a method for identifying test compounds that can be used to treat and prevent neoplasia, including precancerous lesions, with minimal side effects associated with COX inhibition and other non-specific interactions.

In one embodiment of this invention, therefore, the screening method involves determining the COX inhibition activity of a test compound. Because the inventors have discovered a relationship between inhibition of cancer and inhibition of phosphodiesterase Type-V isoenzyme ("PDE-5"), this invention includes determining the PDE-5 inhibition activity of the compound. Preferably, the screening method of this invention further includes determining whether the compounds inhibit the growth of tumor cells in a cell culture.

In an alternate embodiment, the screening method of this invention involves determining the COX inhibition activity of the compound, determining the PDE-5 inhibition activity of the compound and determining whether the compound induces apoptosis in tumor cells.

By screening compounds in this fashion, potentially beneficial and improved compounds can be identified more rapidly and with greater precision than possible in the past. Further benefits will be apparent from the detailed description that follows.

BRIEF DESCRIPTION OF THE DRAWINGS

FIG. 3 illustrates the inhibitory effects of sulindac sulfide and aposulind on PDE-4 and PDE-5 purified from cultured tumor cells.

DETAILED DESCRIPTION OF THE PREFERRED EMBODIMENTS

Figure 1:
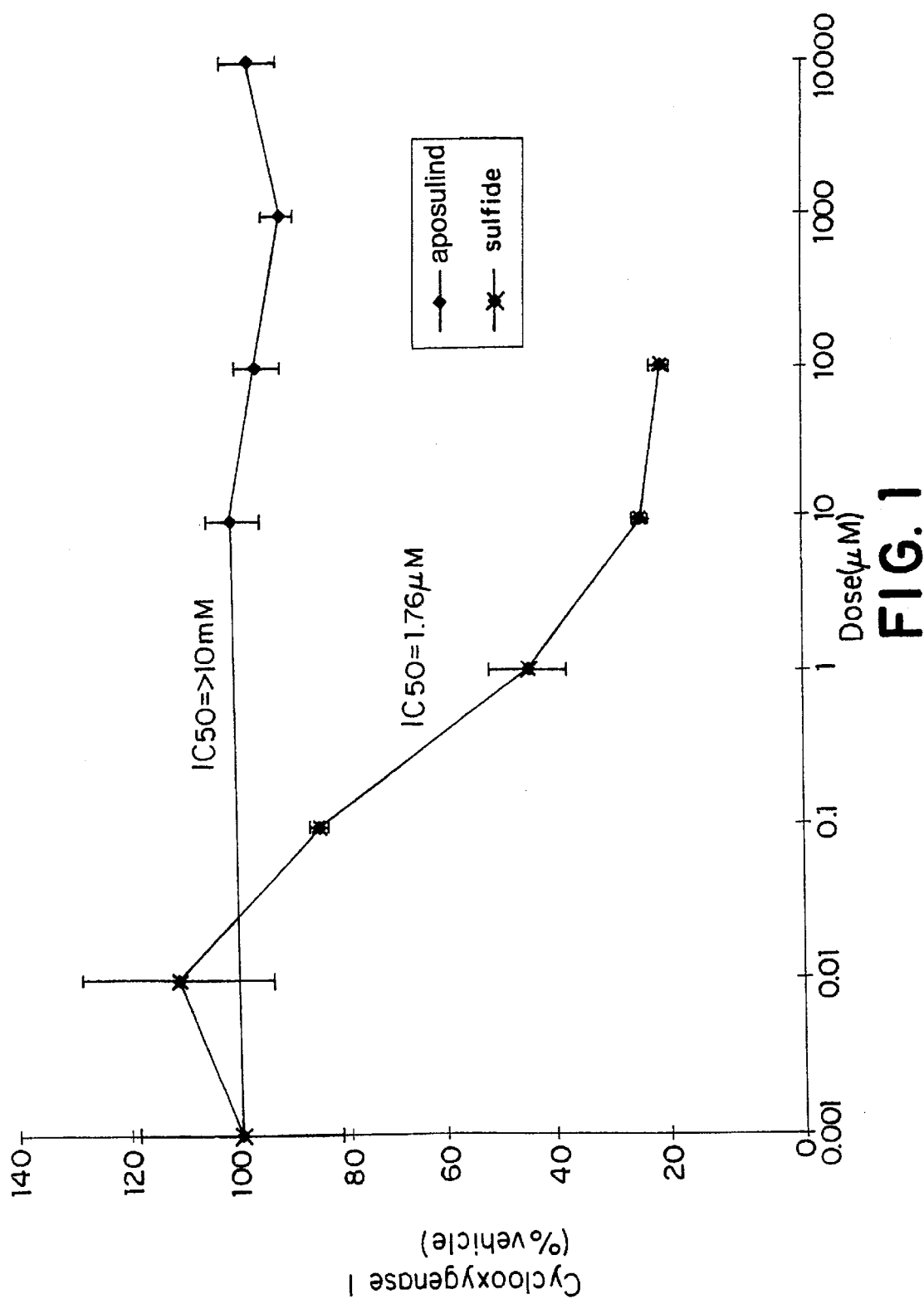
FIG. 1 illustrates the effect of the sulfide derivative of sulindac and the sulfone derivative of sulindac (a.k.a. aposulind) on purified cyclooxygenase activity.

The method of this invention is useful to identify compounds that can be used to treat or prevent neoplasms, and which are not characterized by the serious side effects of conventional NSAIDs.

Cancer and precancer may be thought of as diseases that involve unregulated cell growth. Cell growth involves a number of different factors. One factor is how rapidly cells proliferate, and another involves how rapidly cells die. Cells can die either by necrosis or apoptosis depending on the type of environmental stimuli. Cell differentiation is yet another factor that influences cell growth kinetics. Resolving which of the many aspects of cell growth is affected by a test compound is important to the discovery of a relevant target for pharmaceutical therapy. Screening assays based on this selectivity can be combined with tests to determine which compounds lack the side effects of NSAIDs.

This invention is the product of several important discoveries. First, the present inventors discovered that desirable inhibitors of tumor cell growth induce premature death of cancer cells by apoptosis (see, Piazza, G. A., et al., *Cancer Research,* 55(14), 3110–16, 1995). Second, the present inventors unexpectedly discovered that compounds that selectively induce apoptosis without substantial COX inhibition also inhibit phosphodiesterase ("PDE"). In particular, and contrary to leading scientific studies, desirable compounds for treating neoplastic lesions selectively inhibit Type V isoenzyme form of phosphodiesterase ("PDE-5") (EC 3.1.4.17). PDE-5 is one of seven isoenzymes of phosphodiesterase. PDE-5 is unique in that it selectively degrades cyclic GMP, while the other types of PDE are either non-selective or degrade cyclic AMP. Preferably, desirable compounds do not substantially inhibit other phosphodiesterase types.

A preferred embodiment of the present invention involves determining the cyclooxygenase inhibition activity of a given compound, and determining the PDE-5 inhibition activity of the compound. The test compounds are scored for their probable ability to treat neoplastic lesions either directly by assessing their activities against specific cutoff values or indirectly by comparing their activities against known compounds useful for treating neoplastic lesions. A standard compound that is known to be effective for treating neoplastic lesions without causing gastric irritation is the sulfone metabolite of sulindac: 5-fluoro-2-methyl-1-(p-methylsulfonylbenzylidene)-3-indenylacetic acid ("aposulind"). Other useful compounds for comparative purposes include those that are known to inhibit COX, such as indomethacin and the sulfide metabolite of sulindac: 5-fluoro-2-methyl-1-(p-methylsulfinylbenzylidene)-3-indenylacetic acid ("sulindac sulfide"). Other useful compounds for comparative purposes include those that are known to inhibit PDE-5, such as 1-(3-chloroanilino)-4-phenyphthalazine ("MY5445").

A test compound is clearly determined to be a promising candidate if it performs better than or comparable to the aposulind and does not inhibit COX. In general, desirable compounds are those that inhibit PDE-5 and inhibit cell growth and induce apoptosis, but do not inhibit COX at pharmacologically accepted doses.

As used herein, the term "precancerous lesion" includes syndromes represented by abnormal neoplastic, including dysplastic, changes of tissue. Examples include adenomatous growths in colonic, breast or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), prostatic dysplasia, breast and/or skin and related conditions, whether the lesions are clinically identifiable or not.

As used herein, the term "carcinomas" refers to lesions which are cancerous. Examples include malignant melanomas, breast cancer, prostate cancer and colon cancer. As used herein, the terms "neoplasia" and "neoplasms" refer to both cancerous and pre-cancerous lesions.

As used herein, the abbreviation PG represents prostaglandin, PS represents prostaglandin synthetase; $PGE_2$ represents prostaglandin $E_2$; PDE represents phosphodiesterase; COX represents cyclooxygenase; RIA represents—radioimmunoassay.

In another aspect of the invention, there is a method for treating patients in need of treatment for neoplasia by identifying compounds that exhibit substantial PDE-5 inhibitory activity at pharmacologically acceptable doses, and administering one or more of those compounds to a patient in need thereof with neoplasia sensitive to the compound.

SCREENING PROTOCOLS

The following screening protocols, and alternative protocols, are provided to aid in the understanding of the preferred methods used to screen test compounds to determine their potential to treat or prevent neoplasia, especially pre-cancerous lesions.

1. Determining COX Inhibitory Activity

COX inhibition can be determined by either of two methods. One method involves measuring $PGE_2$ secretion by intact HL-60 cells following exposure to the compound being screened. The other method involves measuring the activity of purified cyclooxygenases (COXs) in the presence of the compound. Both methods involve protocols previously described in the literature.

1.A. $PGE_2$ secretion

Compounds of this can be evaluated to determine whether they inhibited the production of prostaglandin $E_2$ ("$PGE_2$"), according to procedures known in the art. For example, $PGE_2$ secreted from a cell can be measured using an enzyme immunoassay (EIA) kit for $PGE_2$, such as commercially available from Amersham, Arlington Heights, Ill. U.S.A. Suitable cells include those which make an abundance of PG, such as HL-60 cells. HL-60 cells are human promyelocytes that are differentiated with DMSO in mature granulocytes. (See, Collins, S. J., Ruscetti, F. W., Gallagher, R. E. and Gallo, R. C., "Normal Functional Characteristics of Cultured Human Promyelocytic Leukemia Cells (HL-60) After Induction of Differentiation By Dimethylsulfoxide", *J. Exp. Med.,* 149:969–974, 1979). These differentiated cells produce $PGE_2$ after stimulation with a calcium ionophore A23187 (see, Kargman, S., Prasit, P. and Evans, J. F., "Translocation of HL-60 Cell 5-Lipoxygenase", *J. Biol. Chem.,* 266: 23745–23752, 1991). HL-60 are available from the American Type Culture Collection (ATCC:CCL240). They can be grown in a RPMI 1640 medium supplemented with 20% heat-inactivated fetal bovine serum, 50 U/ml penicillin and 50 μg/ml streptomycin in an atmosphere of 5% $CO_2$ at 37° C. To induce myeloid differentiation, cells are exposed to 1.3% DMSO for 9 days and then washed and resuspended in Dulbecco's phosphate-buffered saline at $3\times10^6$ cells/ml.

The differentiated HL-60 cells ($3\times10^6$ cells/ml) can be incubated for 15 min at 37° C. in the presence of the compounds tested at the desired concentration. Cells are then stimulated by A23187 ($5\times10^{-6}$M) for 15 min. $PGE_2$ secreted into the external medium is measured as described above.

1.B Purified cyclooxygenases

Two different forms of cyclooxygenase (COX-1 and COX-2) have been reported in the literature to regulate prostaglandin synthesis. It is known that COX-2 represents the inducible form of COX while COX-1 represents a constitutive form. COX-1 activity can be measured using the method described by Mitchell et al. ("Selectivity of Non-steroidal Anti-inflammatory Drugs as Inhibitors of Constitutive and Inducible Cyclooxygenase," *Proc. Natl. Acad. Sci. USA.,* 90:11693–11697, 1993, which is incorporated herein by reference) using COX-1 purified from ram seminal vesicles as described by Boopathy & Balasubramanian, "Purification And Characterization Of Sheep Platelet Cyclooxygenase" (*Biochem. J.,* 239:371–377, 1988, which is incorporated herein by reference). COX-2 activity can be measured using COX-2 purified from sheep placenta as described by Mitchell et al., 1993, supra.

The cyclooxygenase inhibitory activity of a drug can be determined by methods known in the art. For example, Boopathy & Balasubramanian, 1988, supra, described a procedure in which prostaglandin H synthase 1 (Cayman Chemical, Ann Arbor, Mich.) is incubated at 37° C. for 20 min with 100 μM arachidonic acid (Sigma Chemical Co.), cofactors (such as 1.0 mM glutathione, 1.0 mM hydroquinone, 0.625 μM hemoglobin and 1.25 mM $CaCl_2$ in 100 mM TrisHCl, pH 7.4) and the drug to be tested. Following incubation, the reaction can be terminated with trichloroacetic acid. Enzymatic activity can then be measured spectrophotometrically at 530 nm after stopping the reaction by adding thiobarbituric acid and malonaldehyde.

1.C. Analyzing Results

The amount of inhibition is determined by comparing the activity of the cyclooxygenase in the presence and absence of the test compound. Residual or no COX inhibitory activity (i.e., less than about 25%) at a concentration of about 100 μM is indicative that the compound should be evaluated further for usefulness for treating neoplasia. Preferably, the $IC_{50}$ concentration should be greater than 1000 μM for the compound to be further considered potential use.

2. Determining Phosphodiesterase (PDE-5) Inhibition Activity

Compounds can be screened for inhibitory effect on phosphodiesterase activity using either the enzyme isolated from HT-29 or SW-480 tumor cells, or recombinant HS-PDE-5, for example, or measuring cyclic nucleotide levels in whole cells.

2.A. Purified enzyme

Phosphodiesterase activity can be determined using methods known in the art, such as a method using radioactive $^3$Hcyclic GMP (cGMP)(cyclic 3',5'-guanosine monophosphate) as the substrate for PDE-5 enzyme. (Thompson, W. J., Teraski, W. L., Epstein, P. M., Strada, S. J., *Advances in Cyclic Nucleotide Research,* 10:69–92, 1979, which is incorporated herein by reference). In brief, a solution of defined substrate $^3$H-GMP specific activity (0.2 μM; 100,000 cpm; containing 40 mM Tris-HCl (pH 8.0), 5 mM $MgCl_2$ and 1 mg/ml BSA) is mixed with the drug to be tested in a total volume of 400 μl. The mixture is incubated at 30° C. for 10 minutes with partially purified PDE-5 isolated from HT-29 cells. Reactions are terminated, for example, by boiling the reaction mixture for 75 seconds. After cooling on ice, 100 μl of 0.5 mg/ml snake venom (O. hannah venom available from Sigma) is added and incubated for 10 min at 30° C. This reaction is then terminated by the addition of an alcohol, e.g. 1 ml of 100% methanol. Assay samples are applied to a anion chromatography column (1 ml Dowex, from Aldrich) and washed with 1 ml of 100% methanol. The amount of radioactivity in the breakthrough and the wash from the columns in then measured with a scintillation counter. The degree of PDE-5 inhibition is determined by correlating the amount of radioactivity against a control sample (a reaction mixture lacking the tested compound).

2.B. Cyclic Nucleotide Measurements

Alternatively PDE-5 inhibitory activity may be represented by an increase in the cyclic nucleotide, cGMP. The amount of PDE-5 activity can be determined by assaying for the amount of cyclic nucleotides in the extract of treated cells using radioimmunoassay (RIA). In this procedure, HT-29 or SW-480 cells are plated and grown to confluency. The test compound is then incubated with the cell culture. About 24 to 48 hours thereafter, the culture media is removed and the cells are solubilized. The reaction is stopped by using 0.2N HCl/50% MeOH. A sample is removed for protein assay. Cyclic GMP is purified from the acid/alcohol extracts of cells using anion-exchange chromatography, such as a Dowex column. The cGMP is dried, acetylated according to published procedures, such as using acetic anhydride in triethylamine, (Steiner, A. L., Parker, C. W., Kipnis, D. M., *J Biol. Chem.*, 247(4):1106–13, 1971, which is incorporated herein by reference). The acetylated cGMP is quantitated using radioimmunoassay procedures (Harper, J., Brooker, G., *Advances in Nucleotide Research*, 10:1–33, 1979, which is incorporated herein by reference). Iodinated ligands (tyrosine metheyl ester) of derivatized cyclic GMP are incubated with standards or unknowns in the presence of antisera and appropriate buffers. Antiserum may be produced using cyclic nucleotide-haptene directed techniques. The antiserum is from sheep injected with succinyl-cGMP-albumin conjugates and diluted 1/20,000. Dose-interpolation and error analysis from standard curves are applied as described previously (Seibert, A. F., Thompson, W. J., Taylor, A., Wilbourn, W. H., Barnard, J. and Haynes, J., *J. Applied Physiol.*, 72:389–395, 1992, which is incorporated herein by reference).

In addition to observing increases in content of cGMP caused by desirable test compounds, decreases in content of cAMP have been observed. The change in the ratio of the two cyclic nucleotides may be a more accurate measurement for evaluating desirable PDE-5 inhibition activity of test compounds, rather than measuring only the absolute value of cGMP. It is believed that the mechanism of action of a desirable test compound follows a time course consistent with PDE-5 inhibition as one initial action resulting in an increased cGMP content within minutes. And secondarily, the action leads to decreased cAMP content within 24 hours. The intracellular targets of drug actions are being studied further, but current data supports the concept that both cyclic nucleotide effects precede apoptosis in HT-29 cells. Ratios of cGMP/cAMP are in the 0.03–0.05 range (300–500 fmol/mg cGMP over 6000–8000 fmol/mg cAMP) for both HT-29 and SW-480 cell lines, and have been shown to increase several fold as the result of an initial increase in cyclic GMP and later a decrease in cyclic AMP.

To determine the content of cyclic AMP, radioimmunoassay techniques similar to those described above for cGMP are used. Basically, cyclic nucleotides are purified from acid/alcohol extracts of cells using anion-exchange chromatography, dried, acetylated according to published procedures and quantitated using radioimmunoassay procedures. Iodinated ligands of derivatized cyclic AMP and cyclic GMP are incubated with standards or unknowns in the presence of specific antisera and appropriate buffers.

Verification of the cyclic nucleotide content may be obtained by determining the turnover or accumulation of cyclic nucleotides in intact cells. To measure cAMP, this procedure uses $^3$H-adenine prelabeling according to published procedures (Whalin M. E., R. L. Garrett Jr., W. J. Thompson, and S. J. Strada, "Correlation of cell-free brain cyclic nucleotide phosphodiesterase activities to cyclic AMP decay in intact brain slices", *Sec. Mess. and Phos. Protein Research*, 12:311–325, 1989, which is incorporated herein by reference). The procedure measures flux of labeled ATP to cyclic AMP and can be used to estimate intact cell adenylate cyclase or cyclic nucleotide phosphodiesterase activities depending upon the specific protocol. Cyclic GMP accumulation was too low to be studied with intact cell prelabeling according to published procedures (Reynolds, P. E., S. J. Strada and W. J. Thompson, "Cyclic GMP accumulation in pulmonary microvascular endothelial cells measured by intact cell prelabeling," *Life Sci.*, 60:909–918, 1997, which is incorporated herein by reference).

2.C. Tissue sample assay

The PDE-5 inhibitory activity of a test compound can also be determined from a tissue sample. Tissue samples, such as mammalian (preferably rat) liver, are collected from subjects exposed to the test compound. Briefly, a sample of tissue is homogenized in 500 μl of 6% TCA. A known amount of the homogenate is removed for protein analysis. The remaining homogenate is allowed to sit on ice for 20 minutes to allow for the protein to precipitate. Next, the homogenate is centrifuged for 30 minutes at 15,000 g at 4° C. The supernatant is recovered and the pellet recovered. The supernatant is washed four times with five volumes of water saturated diethyl ether. The upper ether layer is discarded between each wash. The aqueous ether extract is dried in a speed vac. Once dried, the sample can be frozen for future use, or used immediately. The dried extract is dissolved in 500 μl of assay buffer. The amount of PDE-5 inhibition is determined by assaying for the amount of cyclic nucleotides using an enzyme immunoassay (EIA), such as the Biotrak EIA system acetylation protocol (available from Amersham, Arlington Heights, Ill., U.S.A.). Alternatively, RIA procedures as detailed above may be used.

2.D. Analyzing Results

The amount of inhibition is determined by comparing the activity of PDE-5 in the presence and absence of the test compound. Inhibition of PDE-5 activity is indicative that the compound is useful for treating neoplasia. Significant inhibitory activity greater than that of the benchmark, aposulind, preferably greater than 50% at a concentration of 10 μM, is indicative that a compound should be further evaluated for antineoplastic properties. Preferably, the $IC_{50}$ value for PDE-5 inhibition should be less than 50 μM for the compound to be further considered for potential use.

3. Determining Whether A Compound Reduces The Number Of Tumor Cells

In an alternate embodiment, the screening method of the present invention involves further determining whether the compound reduces the growth of tumor cells. Various cell lines can be used in the sample depending on the tissue to be tested. For example, these cell lines include: SW-480—colonic adenocarcinoma; HT-29—colonic adenocarcinoma, A-427—lung adenocarcinoma carcinoma; MCF-7—breast adenocarcinoma; and UACC-375—melanoma line; and DU145—prostrate carcinoma. Cytotoxicity data obtained using these cell lines are indicative of an inhibitory effect on neoplastic lesions. These cell lines are well characterized, and are used by the United States National Cancer Institute in their screening program for new anti-cancer drugs.

3A. Tumor Inhibition in HT-29 Cell Line

A compound's ability to inhibit tumor cell growth can be measured using the HT-29 human colon carcinoma cell line obtained from ATCC (Bethesda, Md.). HT-29 cells have previously been characterized as relevant colon tumor cell culture model (Fogh, J., and Trempe, G. In: *Human Tumor Cells in Vitro*, J. Fogh (eds.), Plenum Press, New York, pp. 115–159, 1975). HT-29 cells are maintained in RPMI media supplemented with 5% fetal serum (Gemini Bioproducts, Inc., Carlsbad, Calif.) and 2 mm glutamine, and 1% antibiotic-antimycotic in a humidified atmosphere of 95% air and 5% $CO_2$ at 37° C. Briefly, HT-29 cells are plated at a density of 500 cells/well in 96 well microtiter plates and incubated for 24 hours at 37° C. prior to the addition of compound. Each determination of cell number involved six replicates. After six days in culture, the cells are fixed by the addition of cold trichloroacetic acid to a final concentration of 10% and protein levels are measured using the sulforhodamine B (SRB) colorimetric protein stain assay as previously described by Skehan, P., Storeng, R., Scudiero, D., Monks, A., McMahon, J., Vistica, D., Warren, J. T., Bokesch, H., Kenney, S., and Boyd, M. R., "New Colorimetric Assay For Anticancer-Drug Screening," *J. Natl. Cancer Inst.* 82: 1107–1112, 1990, which is incorporated herein by reference.

In addition to the SRB assay, a number of other methods are available to measure growth inhibition and could be substituted for the SRB assay. These methods include counting viable cells following trypan blue staining, labeling cells capable of DNA synthesis with BrdU or radiolabeled thymidine, neutral red staining of viable cells, or MTT staining of viable cells.

3.B. Analyzing Results

Significant tumor cell growth inhibition greater than about 50% at a dose of 100 μM is further indicative that the compound is useful for treating neoplastic lesions. Preferably, an $IC_{50}$ value is determined and used for comparative purposes. This value is equivalent to the concentration of drug needed to inhibit tumor cell growth by 50% relative to the control. Preferably, the $IC_{50}$ value should be less than 100 μM for the compound to be considered further for potential use for treating neoplastic lesions.

4. Determining Whether A Compound Induces Apoptosis

In a second alternate embodiment, the screening method of the present invention further involves determining whether the compound induces apoptosis in cultures of tumor cells.

Two distinct forms of cell death may be described by morphological and biochemical criteria: necrosis and apoptosis. Necrosis is accompanied by increased permeability of the plasma membrane; the cells swell and the plasma membrane ruptures within minutes. Apoptosis is characterized by membrane blebbing, condensation of cytoplasm and the activation of endogenous endonucleases.

Of the two, apoptosis is the most common form of eukaryotic cell death. It occurs naturally during normal tissue turnover and during embryonic development of organs and limbs. Apoptosis also is induced by cytotoxic T-lymphocytes and natural killer cells, by ionizing radiation and certain chemotherapeutic drugs. Inappropriate regulation of apoptosis is thought to play an important role in many pathological conditions including cancer, AIDS, Alzheimer disease, etc. Compounds can be screened for induction of apoptosis using cultures of tumor cells maintained under conditions as described above. Treatment of cells with test compounds involves either pre- or post-confluent cultures and treatment for two to seven days at various concentrations. Apoptotic cells are measured in both the attached and "floating" compartments of the cultures. Both compartments are collected by removing the supernatant, trypsinizing the attached cells, and combining both preparations following a centrifugation wash step (10 minutes, 2000 rpm). The protocol for treating tumor cell cultures with sulindac and related compounds to obtain a significant amount of apoptosis has been described in the literature. (See, Piazza, G. A., et al., *Cancer Research*, 55:3110–16, 1995, which is incorporated herein by reference). The novel features include collecting both floating and attached cells, identification of the optimal treatment times and dose range for observing apoptosis, and identification of optimal cell culture conditions.

4.A. Morphological observation of apoptosis

Following treatment with a test compound, cultures can be assayed for apoptosis and necrosis by florescent microscopy following labeling with acridine orange and ethidium bromide. The method for measuring apoptotic cell number has previously been described by Duke & Cohen, "Morphological And Biochemical Assays Of Apoptosis," *Current Protocols In Imnmunology*, Coligan et al., eds., 3.17.1–3.17.16 (1992, which is incorporated herein by reference).

For example, floating and attached cells can be collected by trypsinization and washed three times in PBS. Aliquots of cells can be centrifuged. The pellet can then be resuspended in media and a dye mixture containing acridine orange and ethidium bromide prepared in PBS and mixed gently. The mixture can then be placed on a microscope slide and examined.

4.B. Analysis of apoptosis by DNA fragmentation

Apoptosis can also be quantified by measuring an increase in DNA fragmentation in cells which have been treated with test compounds. Commercial photometric EIA for the quantitative in vitro determination of cytoplasmic histone-associated-DNA-fragments (mono- and oligonucleosomes) are available (Cell Death Detection ELISA$^{okys}$, Cat. No. 1,774,425, Boehringer Mannheim). The Boehringer Mannheim assay is based on a sandwich-enzyme-immunoassay principle using mouse monoclonal antibodies directed against DNA and histones, respectively. This allows the specific determination of mono- and oligonucleosomes in the cytoplasmatic fraction of cell lysates.

According to the vendor, apoptosis is measured in the following fashion. The sample (cell-lysate) is placed into a streptavidin-coated microtiter plate ("MTP"). Subsequently, a mixture of anti-histone-biotin and anti-DNA peroxidase conjugate are added and incubated for two hours. During the incubation period, the anti-histone antibody binds to the histone-component of the nucleosomes and simultaneously fixes the immunocomplex to the streptavidin-coated MTP via its biotinylation. Additionally, the anti-DNA peroxidase antibody reacts with the DNA component of the nucleosomes. After removal of unbound antibodies by a washing step, the amount of nucleosomes is quantified by the peroxidase retained in the immunocomplex. Peroxidase is determined photometrically with ABTS7 (2,2'-Azido-[3-ethylbenzthiazolin-sulfonate])* as substrate.

For example, SW-480 colon adenocarcinoma cells are plated in a 96-well MTP at a density of 10,000 cells per well. Cells are then treated with test compound, and allowed to incubate for 48 hours at 37° C. After the incubation, the MTP is centrifuged and the supernatant is removed. The cell pellet in each well is then resuspended in lysis buffer for 30 minutes. The lysates are then centrifuged and aliquots of the supernatant (i.e. cytoplasmic fraction) are transferred into streptavidin coated MTP. Care is taken not to shake the lysed pellets (i.e. cell nucleii containing high molecular weight, unfragmented DNA) in the MTP. Samples are then analyzed.

Fold stimulation (FS=$OD_{max}/OD_{veh}$), an indicator of apoptotic response, is determined for each compound tested at a given concentration. $EC_{50}$ values may also be determined by evaluating a series of concentrations of the test compound.

4.C. Analyzing Results

Statistically significant increases of apoptosis (i.e., greater than 2 fold stimulation at a concentration of 100 μM) are further indicative that the compound is useful for treating neoplastic lesions. Preferably, the $EC_{50}$ value for apoptotic activity should be less than 100 μM for the compound to be further considered for potential use for treating neoplastic lesions. $EC_{50}$ is herein defined as the concentration that causes 50% induction of apoptosis relative to vehicle treatment.

5. VALIDATION—Mammary Gland Organ Culture Model Tests

Test compounds identified by the above methods can be tested for antineoplastic activity by their ability to inhibit the incidence of preneoplastic lesions in a mammary gland organ culture system. This mouse mammary gland organ culture technique has been successfully used by other investigators to study the effects of known antineoplastic agents such as NSAIDs, retinoids, tamoxifen, selenium, and certain natural products, and is useful for validation of the screening method of the present invention.

For example, female BALB/c mice can be treated with a combination of estradiol and progesterone daily, in order to prime the glands to be responsive to hormones in vitro. The animals are sacrificed and thoracic mammary glands are excised aseptically and incubated for ten days in growth media supplemented with insulin, prolactin, hydrocortisone, and aldosterone. DMBA (7,12-dimethylbenz(a)anthracene), is administered to induce the formation of premalignant lesions. Fully developed glands are then deprived of prolactin, hydrocortisone, and aldosterone, resulting in the regression of the glands but not the premalignant lesions.

The test compound is dissolved in DMSO and added to the culture media for the duration of the culture period. At the end of the culture period, the glands were fixed in 10% formalin, stained with alum carmine, and mounted on glass slides. The incidence of forming mammary lesions is the ratio of the glands with mammary lesions and glands without lesions. The incidence of mammary lesions in test compound treated glands is compared with that of the untreated glands.

The extent of the area occupied by the mammary lesions can be quantitated by projecting an image of the gland onto a digitation pad. The area covered by the gland is traced on the pad and considered as 100% of the area. The space covered by each of the unregressed structures is also outlined on the digitization pad and quantitated by the computer.

EXPERIMENTAL SECTION

A number of test compounds were examined in the various protocols and screened for potential use in treating neoplasia. The results of these tests are reported below. The test compounds are hereinafter designated by a letter code that corresponds to the following:

A—rac-threo-(E)-1-(N,N'-diethylaminoethanethio)-1-(butan-1',4'-olido)-[3',4': 1,2]-6-fluoro-2-methyl-3-(p-methylsulfonylbenzylidene)-indan;

B—(Z)-5-Fluoro-2-methyl-1-(3,4,5-trimethoxybenzylidene)-3-acetic acid;

C—(Z)-5-Fluoro-2-methyl-1-(p-chlorobenzylidene)-3-acetic acid;

D—rac-(E)-1-(butan-1',4'-olido)-[3',4':1,2]-6-fluoro-2-methyl-3-(p-methylsulfonylbenzylidene)-1S-indanyl-N-acetylcysteine;

E—(Z)-5-Fluoro-2-methyl-1-(3,4,5-trimethoxybenzylidene)-3-indenylacetamide, N-benzyl;

F—(Z)-5-Fluoro-2-methyl-1-(p-methylsulfonylbenzylidene)-3-indenylacetamide, N,N'-dicyclohexyl;

G—ribo-(E)-1-Triazolo-[2',3':1",3"]-1-(butan-1',4'-olido)-[3',4':1,2]-6-fluoro-2-methyl-3-(p-methylsulfonylbenzylidene)-indan; and H—rac-(E)-1-(butan-1',4'-olido)-[3',4' ,2]-6-fluoro-2-methyl-3-(p-methylsulfonylbenzylidene)-1S-indanyl-glutathione).

EXAMPLE 1
COX inhibition assay

Reference compounds and test compounds were analyzed for their COX inhibitory activity in accordance with the protocol for the COX assay of section 1.B. supra. FIG. 1 shows the effect of various concentrations of either sulindac sulfide or aposulind on purified cyclooxygenase (Type 1) activity. Cyclooxygenase activity was determined using purified cyclooxygenase from ram seminal vesicles as described previously (Mitchell et al, supra). The IC-50 value for sulindac sulfide was calculated to be approximately 1.76 $\mu$M, while that for sulindac aposulind was greater than 10,000 $\mu$M. These data show that sulindac sulfide, but not aposulind, is a COX-1 inhibitor. Similar data was obtained for the COX-2 isoenzyme. (Thompson, et al., Journal of the National Cancer Institute, 87: 1259–1260, 1995).

Figure 2:
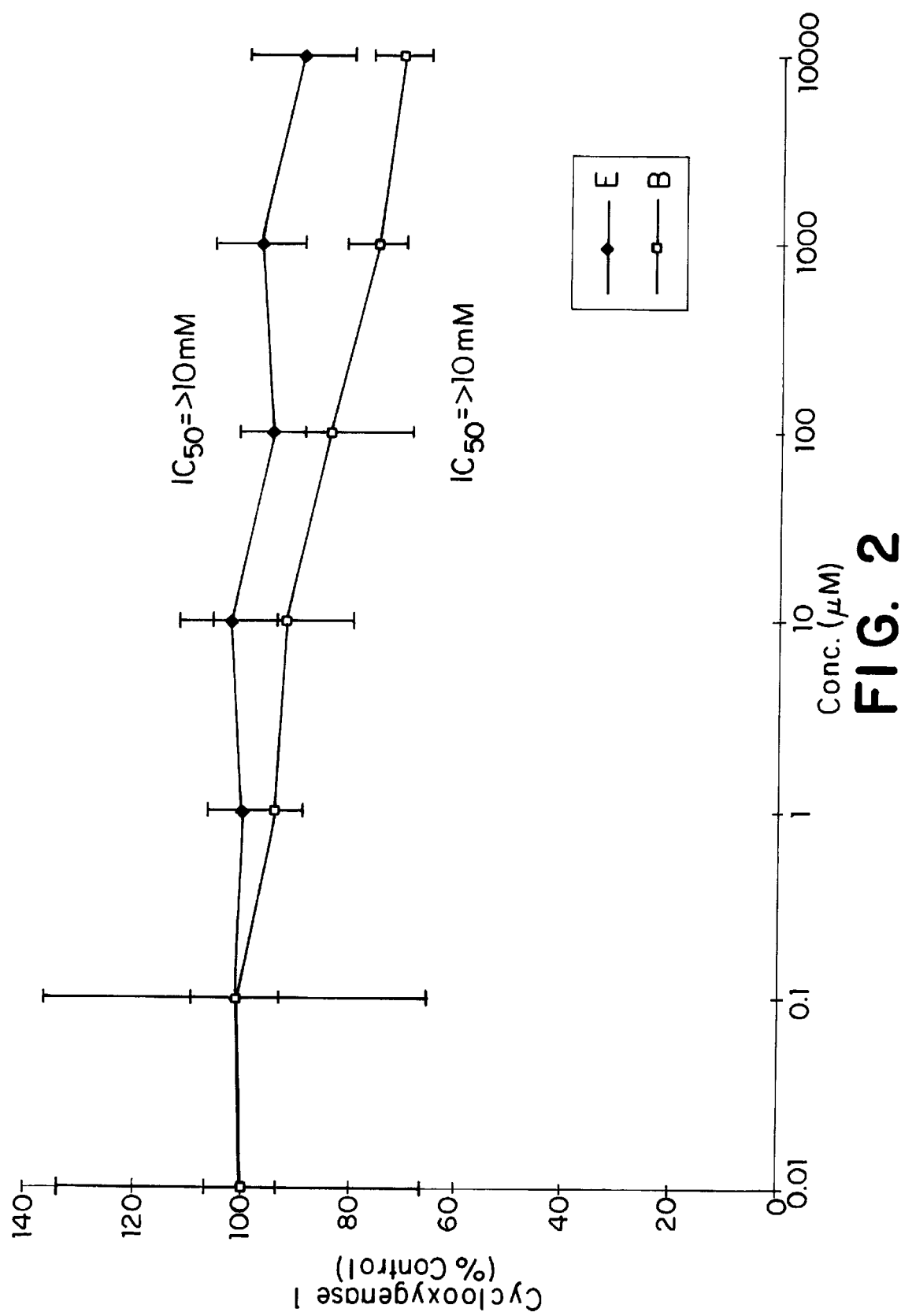
FIG. 2 illustrates the effects of test compounds B and E on COX Inhibition.

FIG. 2 shows the effect of test compounds B and E on COX inhibition. COX activity was determined as for the compounds shown in FIG. 1. The data show that both test compound B and E do not significantly inhibit COX-1.

TABLE 1

Cyclooxygenase inhibitory activity among a series of compounds

|  | % Inhibition at 100 $\mu$M |
|---|---|
| Reference compounds | |
| Indomethacin | 95 |
| MY5445 | 94 |
| Sulindac sulfide | 97 |
| Aposulind | <25 |
| Test compounds | |
| A | <25 |
| B | <25 |
| C | 87 |
| D | <25 |
| E | <25 |

In accordance with the protocol of section 1.B., supra, compounds A through E were evaluated for COX inhibitory activity as reported in Table 1 above. Compound C was found to inhibit COX greater than 25% at a 100 $\mu$M dose, and therefore, would not be selected for further screening.

EXAMPLE 2
PDE-5 inhibition assay

Reference compounds and test compounds were analyzed for their PDE-5 inhibitory activity in accordance with the protocol for the assay of section 2.A., supra. FIG. 3 shows the effect of various concentrations of sulindac sulfide and aposulind on either PDE-4 or PDE-5 activity purified from human colon HT-29 cultured tumor cells, as described previously (W. J. Thompson et al., supra). The $IC_{50}$ value of sulindac sulfide for inhibition of PDE-4 was 41 $\mu$M, and for inhibition of PDE-5 was 17 $\mu$M. The $IC_{50}$ value of aposulind for inhibition of PDE-4 was 181 $\mu$M, and for inhibition of PDE-5 was 56 $\mu$M. These data show that both sulindac sulfide and aposulind inhibit phosphodiesterase activity. Both compounds show selectivity for the PDE-5 isoenzyme form.

Figure 4A:
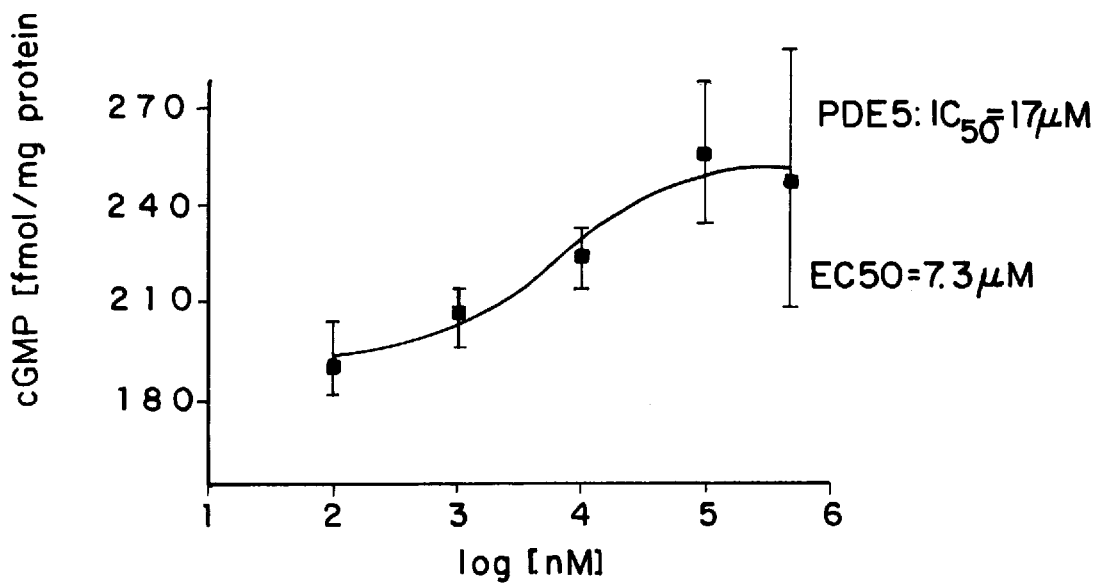
FIGS. 4A and 4B illustrates the effects of sulindac sulfide on cyclic nucleotide levels in HT-29 cells.
Figure 4B:
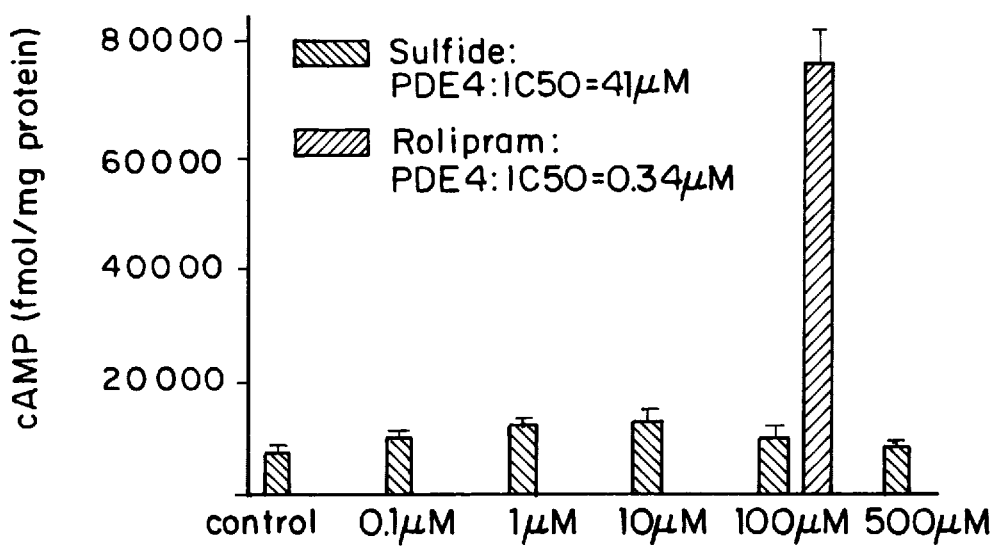

FIG. 4 shows the effects of sulindac sulfide on either cGMP or cAMP production as determined on cultured HT-29 cells in accordance with the assay of section 2.B., supra. HT-29 cells were treated with sulindac sulfide for 30 minutes and cGMP or cAMP was measured by conventional radioimmunoassay method. As indicated, sulindac sulfide increased the levels of cGMP by greater than 50% with an $EC_{50}$ value of 7.3 $\mu$M (top). Levels of cAMP were unaffected by treatment, although a known PDE-4 (Type IV) inhibitor, Rolipram, increased cAMP (bottom). The data demonstrate the pharmacological significance of inhibiting PDE-5 (Type V isoenzyme of phosphodiesterase), relative to PDE-4 (Type IV isoenzyme).

Figure 5:
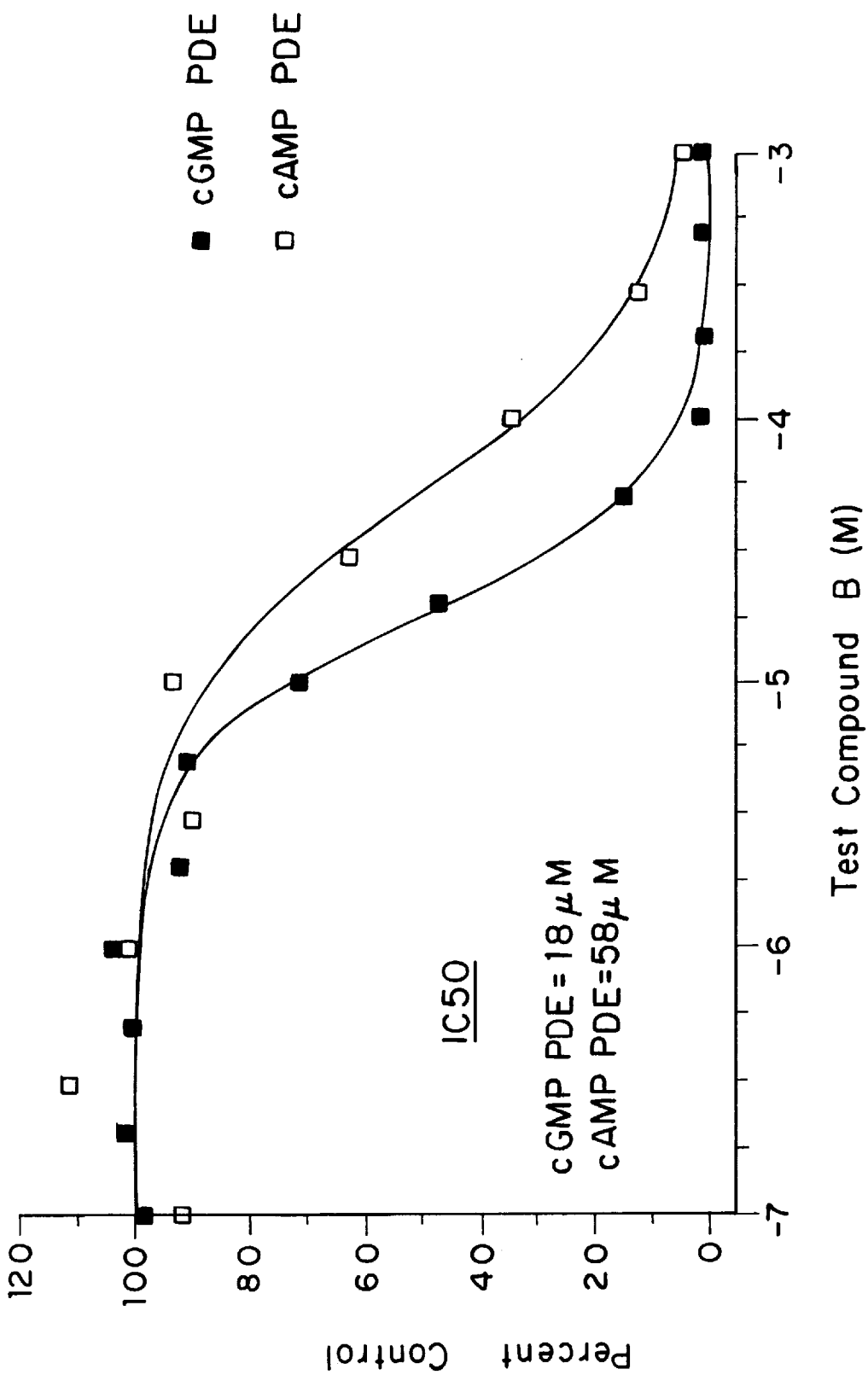
FIG. 5 illustrates the phosphodiesterase inhibitory activity of compound B.

FIG. 5 shows the effect of the indicated dose of test compound B on either PDE-5 (Type V; cGMP PDE) or PDE-4 (Type IV; cAMP PDE) isozymes of phosphodiesterase. The calculated IC$_{50}$ value for PDE-5 was 18 μM and 58 μM for PDE-4.

Figure 6:
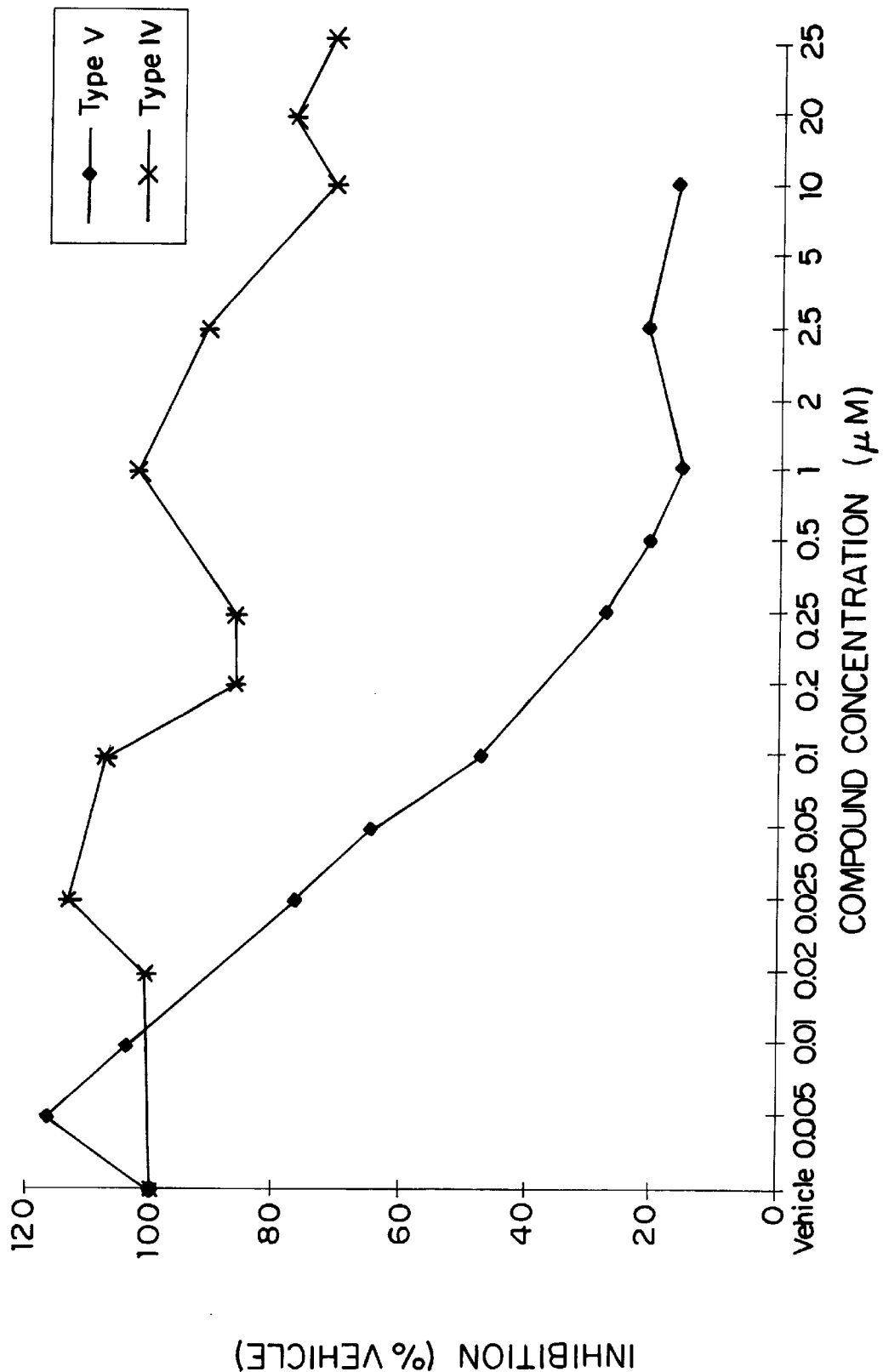
FIG. 6 illustrates the phosphodiesterase inhibitory activity of compound E.

FIG. 6 shows the effect of the indicated dose of test compound E on either PDE-4 or PDE-5. The calculated IC$_{50}$ value was 0.08 μM for PDE-5 and greater than 25 μM for PDE-4.

TABLE 2

PDE-5 inhibitory activity among a series of compounds

|  | % Inhibition at 100 μM |
|---|---|
| Reference compounds |  |
| Indomethacin | 34 |
| MY5445 | 86 |
| Sulindac sulfide | 97 |
| Aposulind | 39 |
| Test compounds |  |
| A | <25 |
| B | <25 |
| C | <25 |
| D | 36 |
| E | 75 |

The above compounds in Table 2 were evaluated for PDE inhibitory activity, as described in the protocol of section 2.A; supra. Of the compounds that did not inhibit COX, only compound E was found to cause greater than 50% inhibition at 10 μM. As noted in FIG. 11, compound B showed inhibition of greater than 50% at a dose of 20 μM. Therefore, depending on the dosage level used in a single dose test, some compounds may be screened out that otherwise may be active at slightly higher dosages. The dosage used is subjective and may be lowered after active compounds are found at certain levels to identify even more potent compounds.

EXAMPLE 3

Apoptosis assay

Figure 7A:
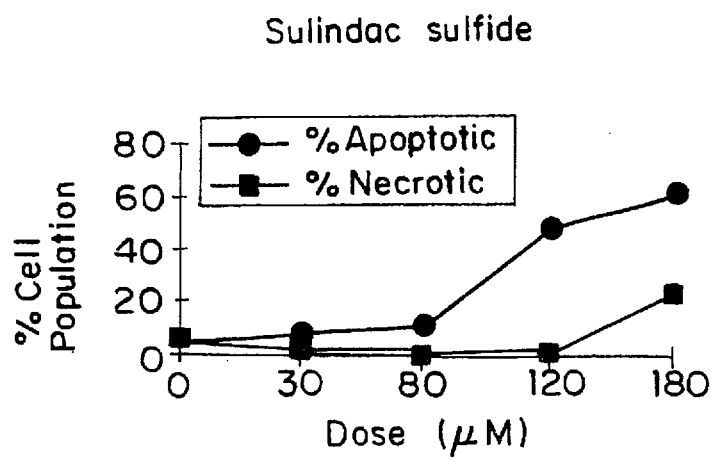
FIGS. 7A and 7B illustrate the effects of sulindac sulfide and aposulind on apoptosis and necrosis of HT-29 cells.
Figure 7B:
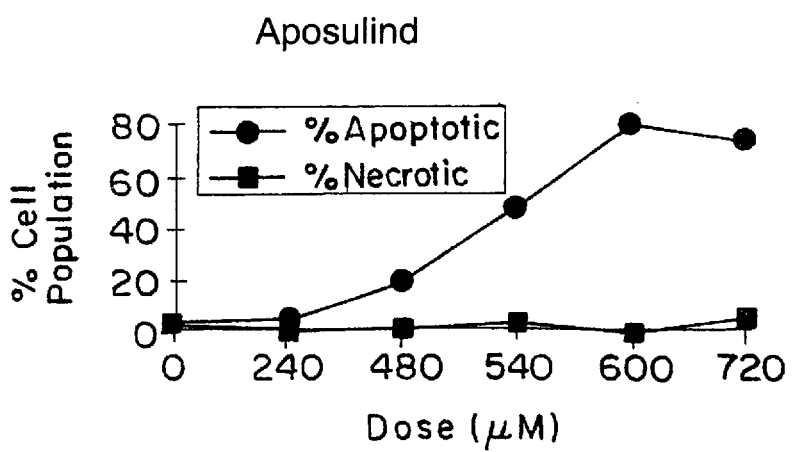

Reference compounds and test compounds were analyzed for their PDE-5 inhibitory activity in accordance with the protocol for the assay of section 4.A. and 4.B., supra. In accordance with the assay of 4.A., FIG. 7 shows the effects of sulindac sulfide and aposulind on apoptotic and necrotic cell death. HT-29 cells were treated for six days with the indicated dose of either sulindac sulfide or aposulind. Apoptotic and necrotic cell death was determined previously (Duke and Cohen, In: Current Protocols in Immunology, 3.17.1–3.17.16, New York, John Wiley and Sons, 1992). The data shows that both sulindac sulfide and aposulind are capable of causing apoptotic cell death without inducing necrosis. All data was collected from the same experiment.

Figure 8A:
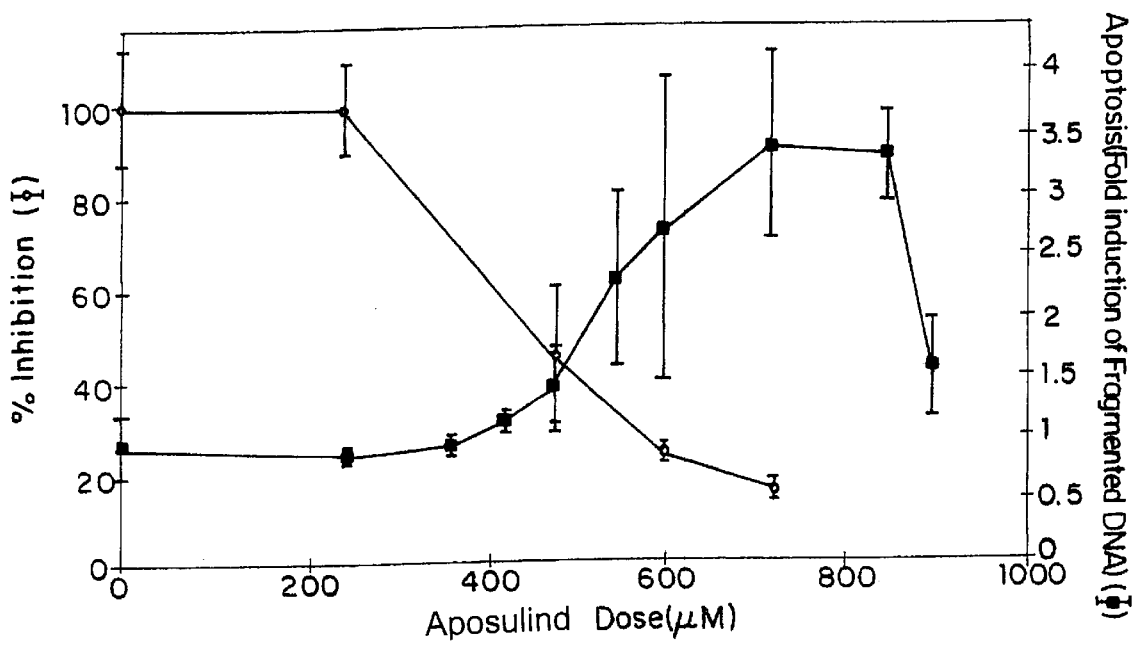
FIGS. 8A and 8B illustrate the effects of sulindac sulfide and aposulind on HT-29 cell growth inhibition and apoptosis induction as determined by DNA fragmentation.
Figure 8B:
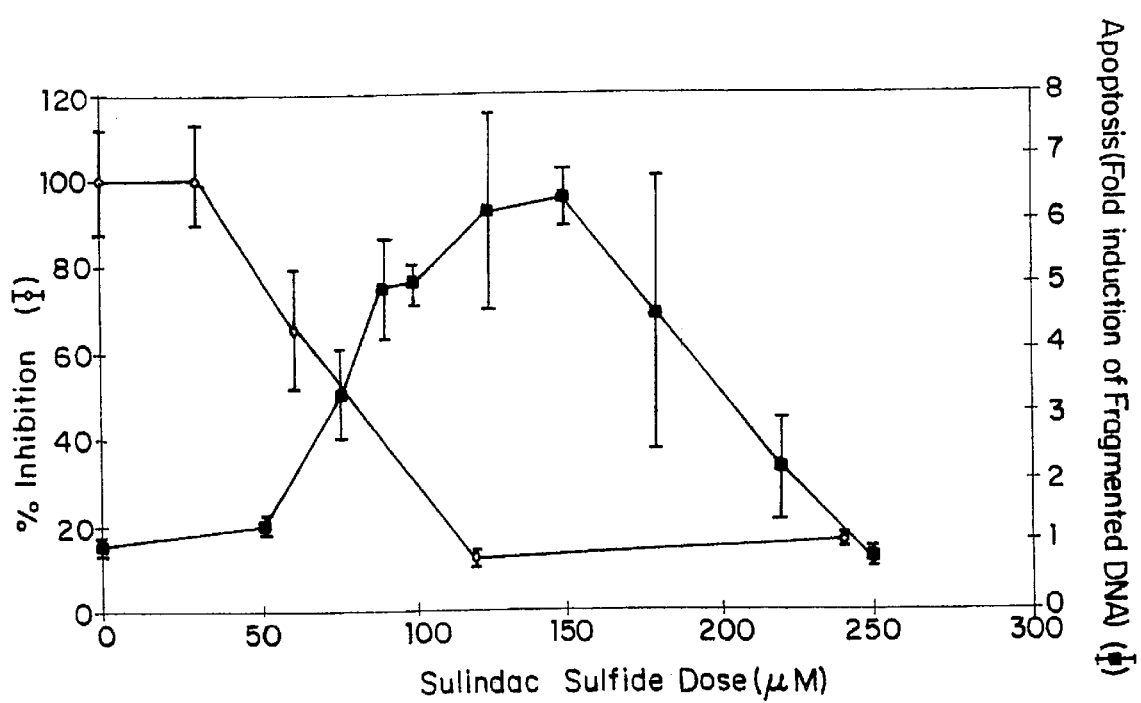

In accordance with the assay of 4.B., FIG. 8 shows the effect of sulindac sulfide and sulfone on tumor growth inhibition and apoptosis induction as determined by DNA fragmentation. Top figure; growth inhibition (open symbols, right axis) and DNA fragmentation (closed symbols, left axis) by aposulind. Bottom figure; growth inhibition (open symbols) and DNA fragmentation (closed symbols) by sulindac sulfide. Growth inhibition was determined by the SRB assay after six days of treatment. DNA fragmentation was determined after 48 hours of treatment. All data was collected from the same experiment.

Figure 9:
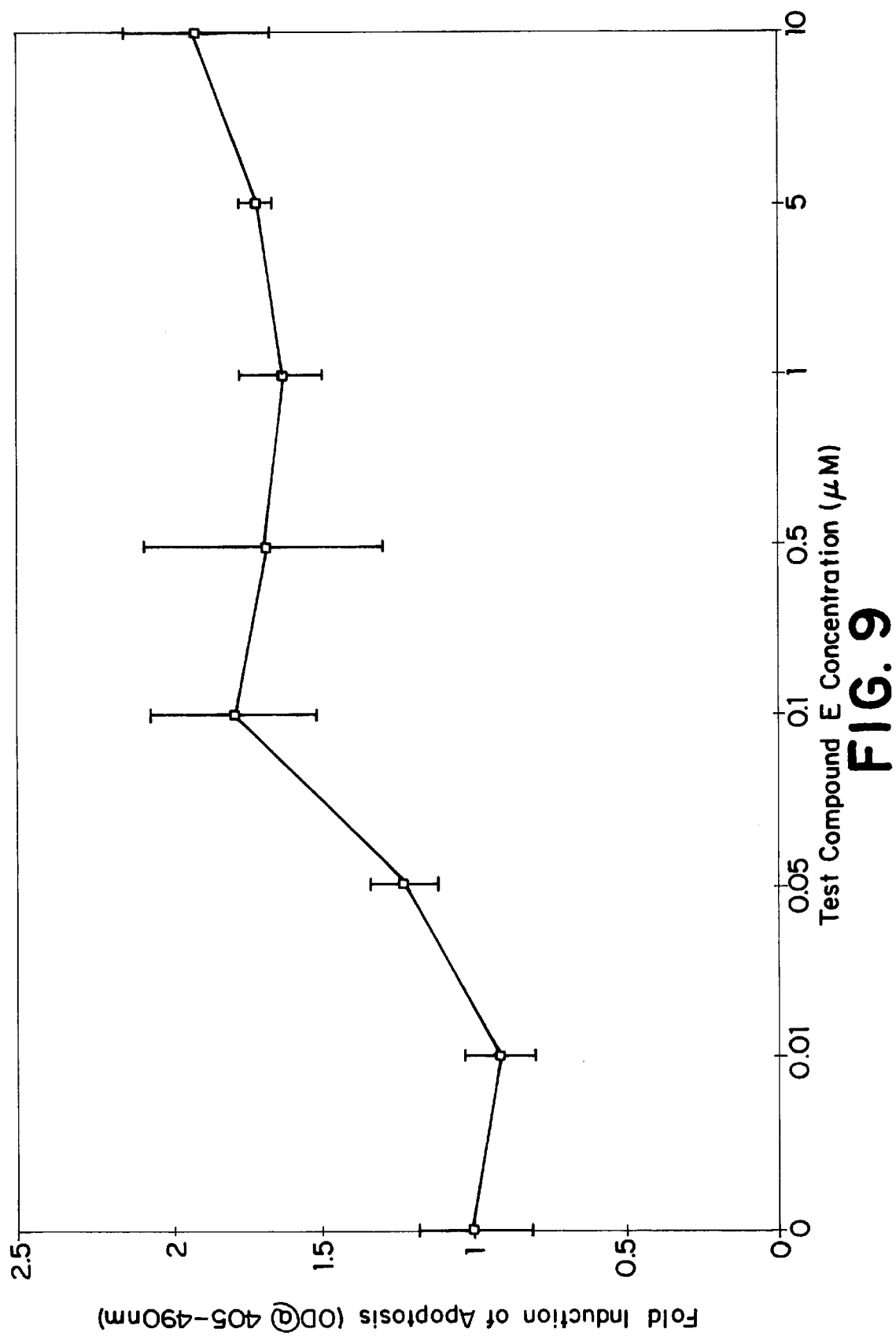
FIG. 9 illustrates the apoptosis inducing properties of compound E.

FIG. 9 shows the apoptosis inducing properties of compound E HT-29 colon adenocarcinoma cells were treated with the indicated concentration of compound E for 48 hours and apoptosis was determined by the DNA fragmentation assay. The calculated EC$_{50}$ value was 0.05 μM.

Figure 10:
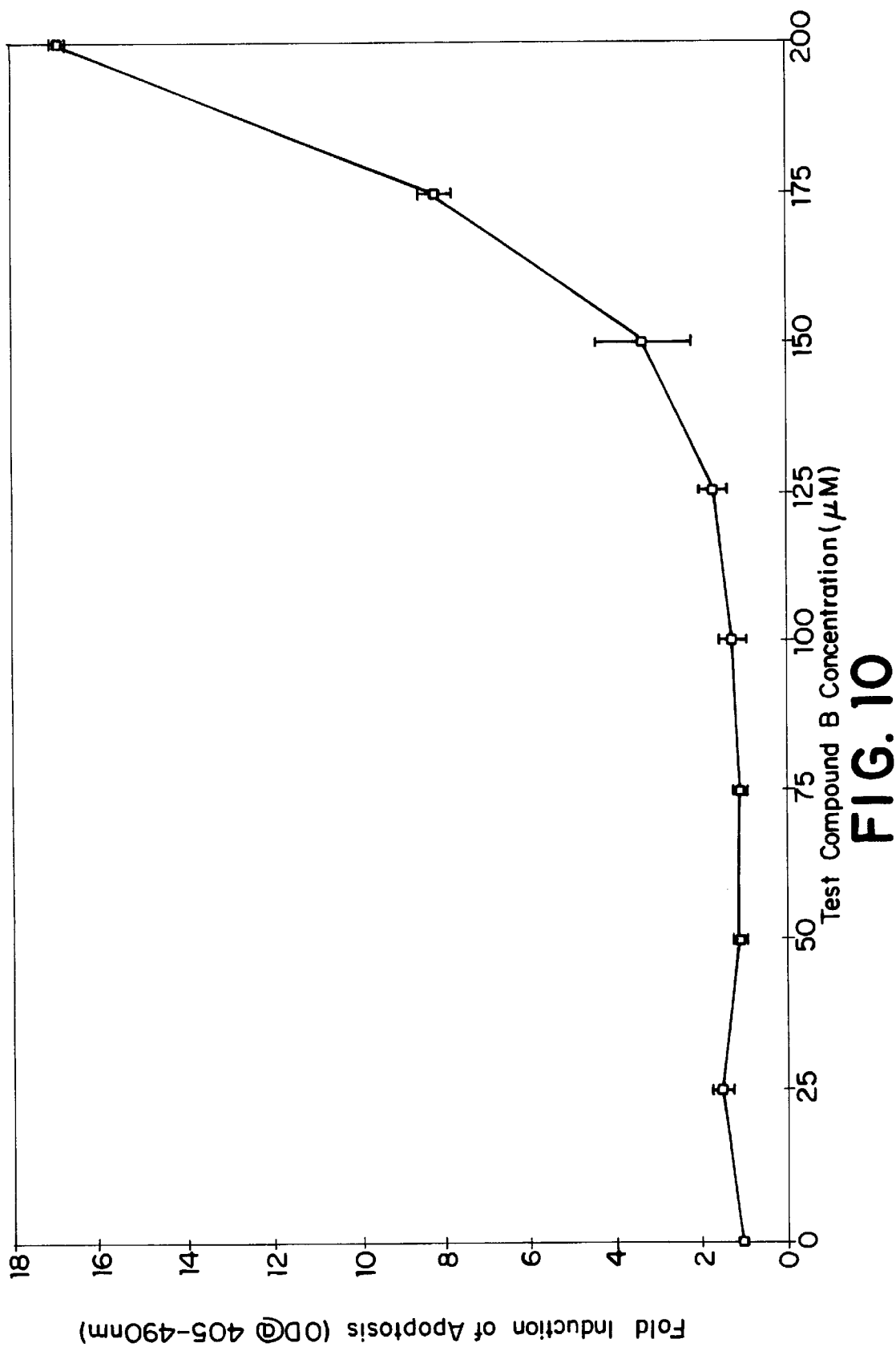
FIG. 10 illustrates the apoptosis inducing properties of compound B.

FIG. 10 shows the apoptosis inducing properties of compound B HT-29 colon adenocarcinoma cells were treated with the indicated concentration of compound B for 48 hours and apoptosis was determined by the DNA fragmentation assay. The calculated EC$_{50}$ value was approximately 175 μM.

TABLE 3

Apoptosis inducing activity among a series of compounds

| Reference compounds | Fold induction 100 μM |
|---|---|
| Indomethacin | <2.0 |
| MY5445 | 4.7 |
| Sulindac sulfide | 7.9 |
| Aposulind | <2.0 |
| Test compounds | Fold induction at 100 μM |
| A | <2.0 |
| B | 3.4 |
| C | 5.6 |
| D | <2.0 |
| E | 4.6 |

In accordance with the protocol of section 4.B., supra, the compounds A through E were tested for apoptosis inducing activity, as reported in Table 3 above. Compounds B, C and E showed significant apoptotic inducing activity, greater than 2.0 fold, at a dosage of 100 μM. Of these three compounds, at this dosage only B and E did not inhibit COX and inhibited PDE-5.

The apoptosis inducing activity for a series of phosphodiesterase inhibitors was determined. The data are shown in Table 4 below. HT-29 cell were treated for 6 days with various inhibitors of phosphodiesterase. Apoptosis and necrosis were determined morphologically after acridine orange and ethidium bromide labelling in accordance with the assay of section 4.A., supra. The data shows that only Type V inhibitors were effective for inducing apoptosis of HT-29 cells.

TABLE 4

Apoptosis Inducing Data for PDE Inhibitors

| Inhibitor | Selectivity | % Apoptosis | % Necrosis |
|---|---|---|---|
| Vehicle |  | 8 | 6 |
| 8-methoxy-IBMX | Type I | 2 | 1 |
| Milrinone | Type III | 18 | 0 |
| RO-20-1724 | Type IV | 11 | 2 |
| MY5445 | Type V | 80 | 5 |
| IBMX | Non-selective | 4 | 13 |

EXAMPLE 4

Growth inhibition assay

Figure 11:
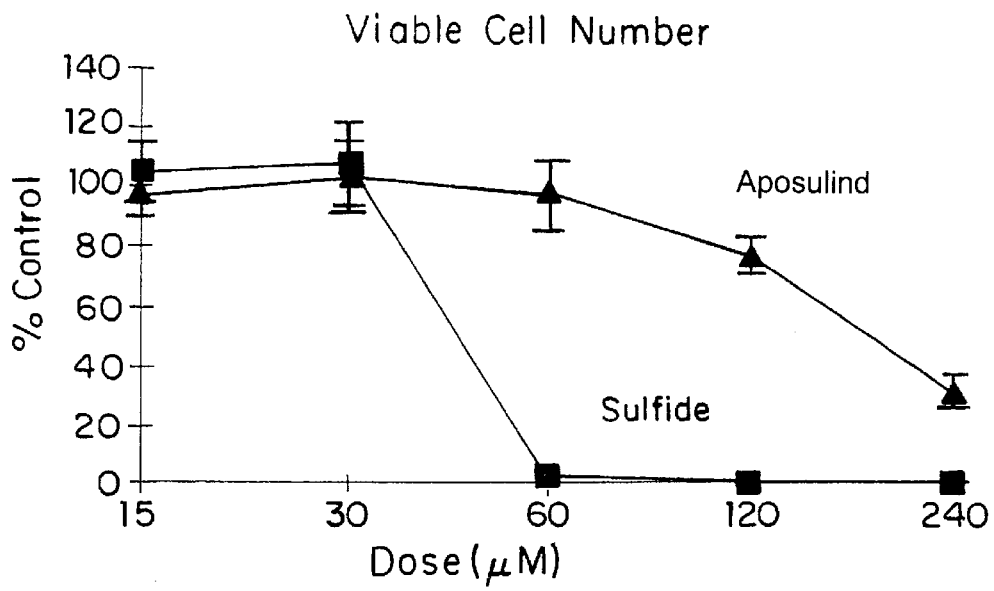
FIG. 11 illustrates the effects of sulindac sulfide and apolulind on tumor cell growth.

Reference compounds and test compounds were analyzed for their PDE-5 inhibitory activity in accordance with the protocol for the assay of section 3.A., supra. FIG. 11 shows the inhibitory effect of various concentrations of sulindac sulfide and aposulind on the growth of HT-29 cells. HT-29 cells were treated for six days with various doses of aposulind (triangles) or sulfide (squares) as indicated. Cell number was measured by a sulforhodamine assay as previously described (Piazza et al., *Cancer Research*, 55: 3110–3116, 1995). The IC$_{50}$ value for the sulfide was approximately 45 μM and 200 μM for the sulfone. The data shows that both sulindac sulfide and aposulind are capable of inhibiting tumor cell growth.

Figure 12A:
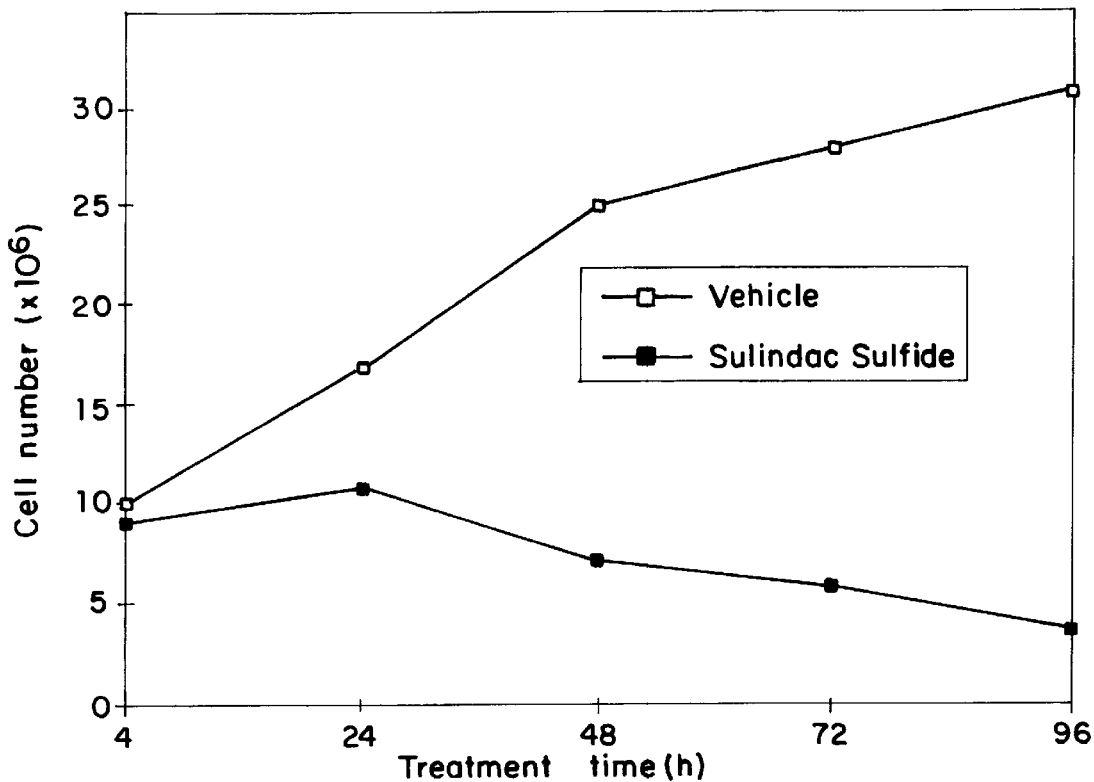
FIGS. 12A and 12B illustrate the growth inhibitory and apoptosis-inducing activity of sulindac sulfide and control (DMSO).
Figure 12B:
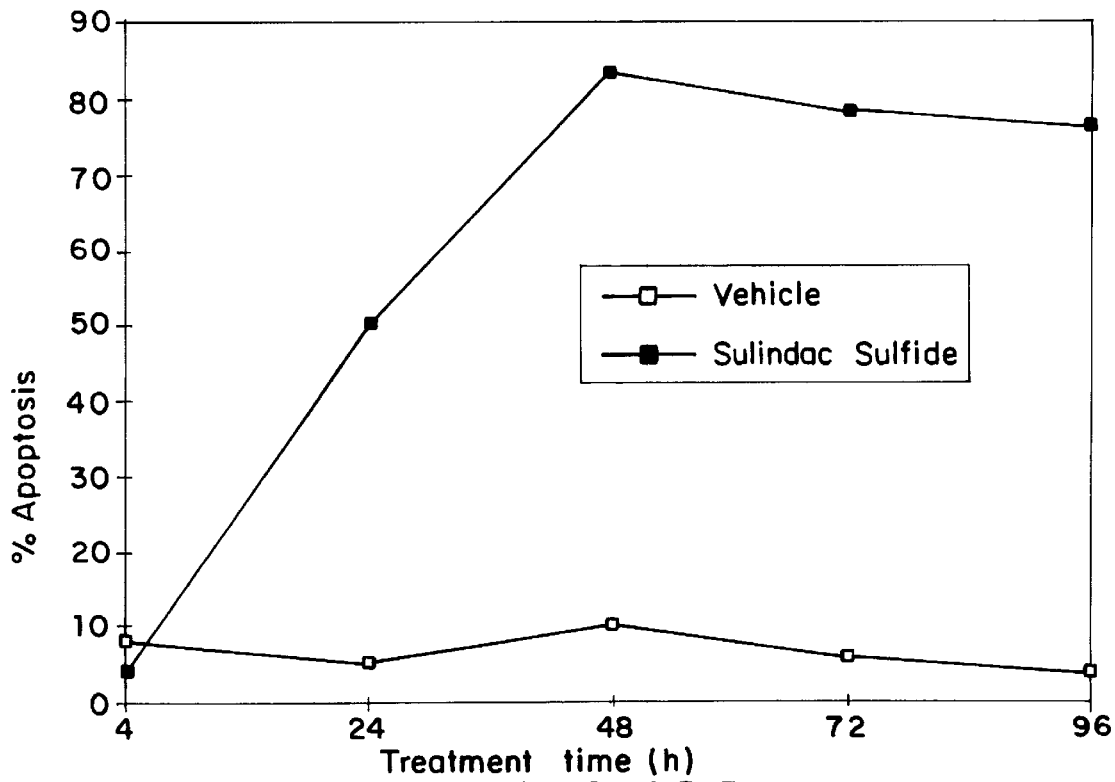

FIG. 12 shows the growth inhibitory and apoptosis-inducing activity of sulindac sulfide. A time course experiment is shown involving HT-29 cells treated with either vehicle, 0.1% DMSO (open symbols) or sulindac sulfide, 120 μM (closed symbols). Growth inhibition (top) was measured by counting viable cells after trypan blue staining. Apoptosis (bottom) was measured by morphological determination following staining with acridine orange and ethidium bromide as described previously (Duke and Cohen, In: Current Protocols in Immunology, 3.17.1–3.17.16, New York, John Wiley and Sons, 1992). The data demonstrate that sulindac sulfide is capable of inhibiting tumor cell growth and that the effect is accompanied by an increase in apoptosis. All data were collected from the same experiment.

Figure 13:
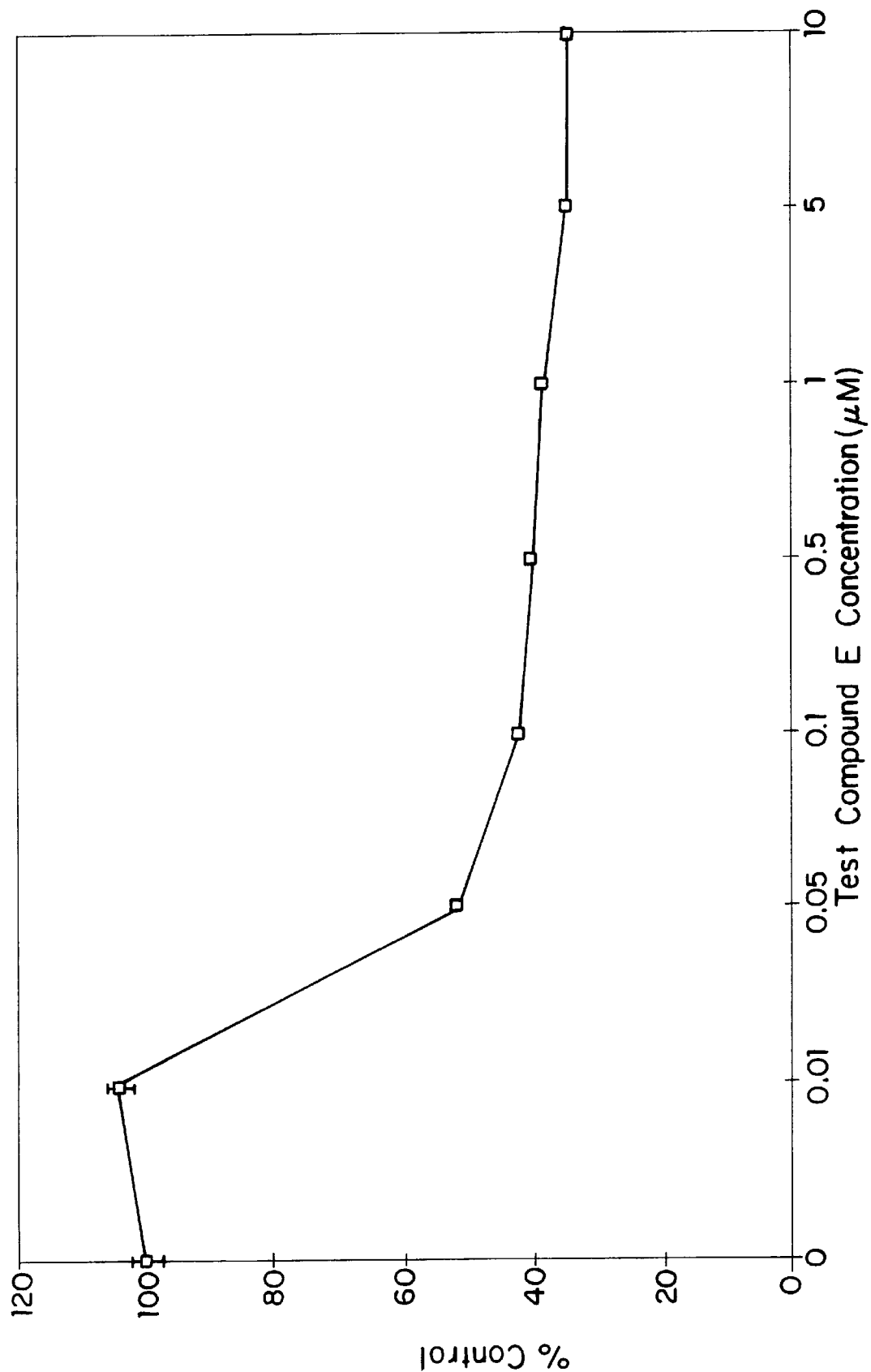
FIG. 13 illustrates the growth inhibitory activity of compound E.

FIG. 13 shows the growth inhibitory activity of test compound E. HT-29 colon adenocarcinoma cells were treated with the indicated concentration of compound E for six days and cell number was determined by the SRB assay. The calculated $IC_{50}$ value was 0.04 μM.

TABLE 5

Growth inhibitory activity among a series of compounds

| Reference compounds 100 μM | % Inhibition at |
|---|---|
| Indomethacin | 75 |
| MY5445 | 88 |
| Sulindac sulfide | 88 |
| Aposulind | <50 |

| Test compounds | % Inhibition at 100 μM |
|---|---|
| A | 68 |
| B | 77 |
| C | 80 |
| D | 78 |
| E | 62 |

In accordance with the screening protocol of section 3.A., supra, compounds A through E were tested for growth inhibitory activity, as reported in Table 5 above. All the test compounds showed activity exceeding the benchmark aposulind at a 100 μM single does test.

The growth inhibitory activity for a series of phosphodiesterase inhibitors was determined. The data are shown in Table 6 below. HT-29 cell were treated for 6 days with various inhibitors of phospohodiesterase. Cell growth was determined by the SRB assay in accordance with section 3.A., supra. The data shows that only inhibitors of PDE-5 were effective for inhibiting tumor cell growth.

TABLE 6

Growth Inhibitory Data for PDE Inhibitors

| Inhibitor | Selectivity | Growth inhibition ($IC_{50}$, μM) |
|---|---|---|
| 8-methoxy-IBMX | Type I | >200 μM |
| Milrinone | Type III | >200 μM |
| RO-20-1724 | Type IV | >200 μM |
| MY5445 | Type V | 5 μM |
| IBMX | Non-selective | >100 μM |

To show the effectiveness of this screening method on various forms of neoplasia, compounds were tested on numerous cell lines. The effects of sulindac sulfide and aposulind on various cell lines was determined. The data is shown in table 7 below. The $IC_{50}$ values were determined by the SRB assay. The data shows the broad effectiveness of these compounds on a broad range of neoplasia, with effectiveness at comparable dose range. Therefore, compounds identified by this invention should be useful for treating multiple forms of neoplasia.

TABLE 7

Growth Inhibitory Data of Various Cell Lines

| Cell Type/ | $IC_{50}$ (μM) | |
|---|---|---|
| Tissue specificity | Sulindac sulfide | Aposulind |
| HT-29, Colon | 60 | 120 |
| HCT116, Colon | 45 | 90 |
| MCF7/S, Breast | 30 | 90 |
| UACC375, Melanoma | 50 | 100 |
| A-427, Lung | 90 | 130 |
| Bronchial Epithelial Cells (normal) | 30 | 90 |
| NRK, Kidney (normal) | 50 | 180 |
| KNRK, Kidney (transformed) | 60 | 240 |

EXAMPLE 5

Activity in mammary gland organ culture model

Figure 14:
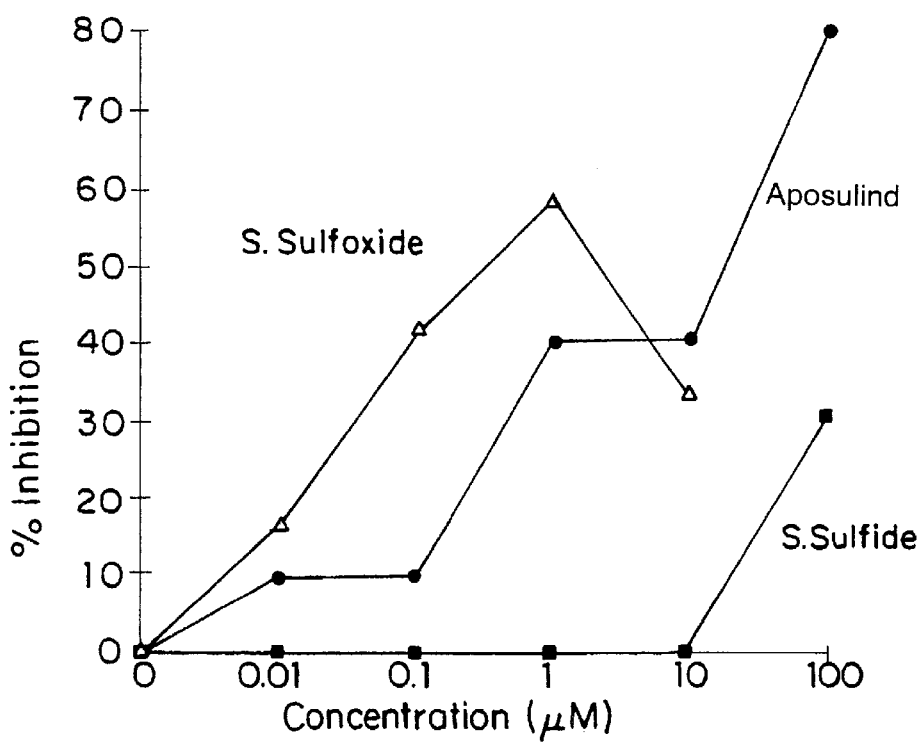
FIG. 14 illustrates the inhibition of premalignant lesions in mouse mammary gland organ culture by sulindac metabolites.

FIG. 14 shows the inhibition of premalignant lesions in mammary gland organ culture by sulindac metabolites. Mammary gland organ culture experiment were performed as previously described (Mehta and Moon, *Cancer Research*, 46: 5832–5835, 1986). The results demonstrate that sulindac aposulind and sulfone effectively inhibit the formation of premalignant lesions, while sulindac sulfide was inactive. The data support the hypothesis that cyclooxygenase inhibition is not necessary for the anti-neoplastic properties of sulindac metabolites.

ANALYSIS

To identify compounds that have potential use for treating neoplasia, this invention provides a rationale for comparing experimental data of test compounds from several protocols. Within the framework of this invention, test compounds can be ranked according to their potential use for treating neoplasia in humans. Those compounds having desirable effects may be selected for more expensive and time consuming animal studies that are required to get approval before initiating human clinical trials.

Qualitative data of various test compounds and the several protocols are shown in Table 8 below. The data show that aposulind, compound B and compound E exhibit the appropriate activity to pass the screen of four assays: lack of COX inhibition, PDE inhibition, growth inhibition and apoptosis induction. The activity of these compounds in the mammary gland organ culture validates the effectiveness of this invention. The qualitative valuations of the screening protocols rank compound E best, then compound B and then aposulind.

TABLE 8

Activity Profile of Various Compounds

| Compound | COX Inhibition | PDB-5 Inhibition | Growth Inhibition | Apoptosis | Mammary Gland Organ Culture |
|---|---|---|---|---|---|
| Aposulind | − | ++ | ++ | ++ | +++ |
| Sulindac sulfide | ++++ | +++ | +++ | +++ | − |
| MY5445 | ++++ | +++ | +++ | +++ | + |

TABLE 8-continued

Activity Profile of Various Compounds

| Com-pound | COX Inhibition | PDB-5 Inhibition | Growth Inhibition | Apoptosis | Mammary Gland Organ Culture |
|---|---|---|---|---|---|
| A | − | − | +++ | ++ | ++ |
| B | − | +++ | +++ | +++ | ++ |
| D | − | − | ++ | − | − |
| E | − | ++++ | ++++ | ++++ | ++++ |
| F | − | − | ++ | + | − |
| G | − | − | +++ | ++ | +++ |
| H | − | − | ++ | − | − |

Table 8 Code:
Activity of compounds based on evaluating a series of experiments involving tests for maximal activity and potency.
− Not active
+ Slightly active
++ Moderately active
+++ Strongly active
++++ Highest activity ever recorded Obviously, numerous modifications and variations of the present invention are possible in light of the above teachings. It is therefore to be understood that within the scope of the appended claims, the invention may be practiced otherwise than as specifically described herein.

What is claimed is:

1. A method for identifying a compound with potential for treating neoplasia, comprising
   determining cyclooxygenase (COX) inhibitory activity of the compound; and
   determining the PDE-5 inhibition activity of said compound;
   wherein low COX inhibitory activity and high inhibition of PDE-5 activity identifies that the compound has potential for treating neoplasia.

2. The method of claim 1, further comprising
   determining whether the compound inhibits tumor cell growth in a culture;
   wherein inhibition of tumor cell growth identifies that the compound has potential for treating neoplasia.

3. The method of claim 1, wherein the COX inhibitory activity of the compound is determined by:
   contacting the compound with purified cyclooxygenase; and
   measuring the change, if any, of cyclooxygenase activity;
   wherein COX inhibitory activity of less than 25% at a concentration of about 100 $\mu$M of the compound further identifies is indicative that the compound has potential for treating neoplasia.

4. The method of claim 1, wherein the COX inhibitory activity of the compound is determined by:
   contacting the compound with a cell which secretes PGE-2; and measuring the decrease, if any, of the PGE-2 secretion from the cell;
   wherein a decrease in PGE-2 secretion correlates to a decrease in prostaglandin synthetase activity.

5. The method of claim 1, further comprising determining whether the compound induces apoptosis of a tumor cell;
   wherein induction of apoptosis further identifies that the compound has potential for treating neoplasia.

6. The method of claim 5, further comprising
   determining whether the compound inhibits tumor cell growth;
   wherein inhibition of tumor cell growth is further indicative that the compound has potential for treating neoplasia.

7. The method of claim 5, wherein PDE-5 activity is determined by;
   contacting the compound with a cell culture; and
   determining the intracellular cyclic GMP concentration in the cell culture;
   wherein PDE-5 inhibitory activity greater than 50% at a concentration of 10 $\mu$M of the compound is indicative that a compound has potential for treating neoplasia.

8. The method of claim 5, wherein PDE-5 activity is determined by:
   determining the ratio of intracellular cyclic GMP/cyclic AMP concentration of the cell;
   wherein a ratio increase greater than three-fold prior to exposure of the compound at a concentration of 10 $\mu$M of the compound is indicative that a compound has potential for treating neoplasia.

9. The method of claim 5, wherein apoptosis is determined by:
   contacting the compound with a cell culture; and
   determining if the compound increases an amount of fragmented DNA in the cytoplasm of the cell;
   wherein increases of apoptosis of greater than 2 fold stimulation prior to exposure of the compound at a concentration of 100 $\mu$M of the compound are further indicative that the compound has potential for treating neoplasia.

10. A method of selecting compounds potentially useful for treating of neoplasia, comprising
    determining the neoplastic growth inhibitory activity of the compound;
    determining the PDE-5 inhibition activity of the compound; and
    selecting compounds for treating neoplasia that exhibit growth inhibitory activity and PDE-5 inhibitory activity.

11. The method of claim 10, further comprising
    identifying compounds where the $IC_{50}$ value for neoplastic cell growth inhibitory activity is less than about 100 $\mu$M of the compounds.

12. The method of claim 10, further comprising
    determining whether the compound induces apoptosis in a cell; and
    selecting compounds that induce apoptosis.

13. The method of claim 12, further comprising
    selecting compounds where the $EC_{50}$ value for apoptotic activity is less than about 100 $\mu$M.

14. The method of claim 10, further comprising:
    determining whether the cyclooxygenase (COX) inhibitory activity of the compound; and
    selecting compounds with low cyclooxygenase (COX) inhibitory activity relative to PDE-5 inhibitory activity.

15. The method of claim 14, wherein the COX inhibitory activity of said compound is determined by:
    contacting said compound with a cyclooxygenase; and
    measuring the change, if any, of cyclooxygenase.

16. The method of claim 14, wherein the COX inhibitory activity of the compound is determined by:
    contacting the compound with a cell which secretes PGE-2; and
    measuring the decrease, if any, of the PGE-2 secretion from the cell,;
    wherein a decrease in PGE-2 secretion correlates to a decrease in prostaglandin synthetase activity.

17. A method for identifying compounds potentially useful for administering to patients in need of treatment for neoplasia, comprising the steps of:

determining the COX inhibitory activity of the compounds;

determining the phosphodiesterase Type V inhibitors activity of the compounds; and identifying those compounds for potential use in treating neoplasia in patients in need thereof if the compounds exhibit phosphodiesterase Type V inhibitory activity and have low COX inhibitory activity.

18. The method of claim 17 further comprising determining the neoplastic cell growth inhibitory activity of the compounds; and identifying those compounds with phosphodiesterase inhibitory activity substantially greater than COX inhibitory activity at concentrations exhibiting substantial growth inhibitory activity.

19. The method of claim 17 wherein the neoplastic cell growth inhibitory activity is determined by ascertaining the level of apoptosis in a neoplastic cell culture sample.

20. A method for selecting compounds with potential for treating neoplasia comprising determining the phosphodiesterase Type V inhibitory activity of said compounds and selecting compounds with inhibitory activity.

21. The method of claim 20 further comprising determining whether the compounds induce apoptosis in a cell and further selecting compounds with apoptotic inducing activity.

22. The method of claim 21 further comprising determining whether the compounds inhibit prostaglandin synthesis and further selecting compounds with prostaglandin inhibitory activity less than a predetermined value.

23. The method of claim 21 wherein PDE-5 inhibitory activity is determined by measuring the intracellular cyclic GMP and cyclic AMP in a cell and calculating an increase of the ratio of cyclic GMP to cyclic AMP.

24. A method for identifying a compound with potential for treating neoplasia, comprising:

determining the cyclooxygenase-I inhibiting activity of the compound; and determining the phosphodiesterase type 5 inhibiting activity of the compound;

wherein low cyclooxygenase-I inhibiting activity and high inhibition of phosphodiesterase type 5 activity identifies that a compound has potential for treating neoplasia.

25. A method for identifying a compound with potential for treating neoplasia, comprising:

treating neoplastic cells with the compound;

determining the intracellular amount of cGMP in the treated and untreated cells;

determining the intracellular amount of cAMP in the treated and untreated cells;

wherein an increase in the ratio of cGMP/cAMP in the treated cells compared to the ratio of cGMP/cAMP in untreated neoplastic cells identifies that the compound has potential for treating neoplasia.

26. A method for identifying a compound with potential for treating neoplasia, comprising:

selecting a compound with PDE-5 inhibiting activity; and evaluating said neoplastic cell growth inhibiting activity of the compound wherein a compound that has PDE-5 inhibiting activity and neoplastic cell growth inhibiting activity has the potential to inhibit neoplasia without substantially inhibiting the growth of normal cells.

\* \* \* \* \*